United States Patent [19]
Yoon

[11] Patent Number: 5,360,405
[45] Date of Patent: Nov. 1, 1994

[54] AUTOMATIC RETRACTABLE SAFETY PENETRATING INSTRUMENT

[76] Inventor: InBae Yoon, 2101 Highland Ridge Dr., Phoenix, Md. 21131

[21] Appl. No.: 929,338

[22] Filed: Aug. 14, 1992

Related U.S. Application Data

[63] Continuation-in-part of Ser. No. 800,507, Nov. 27, 1991, and a continuation-in-part of Ser. No. 805,506, Dec. 6, 1991, and a continuation-in-part of Ser. No. 808,325, Dec. 16, 1991, Pat. No. 5,324,260, and a continuation-in-part of Ser. No. 848,838, Mar. 10, 1992, and a continuation-in-part of Ser. No. 868,566, Apr. 15, 1992, Pat. No. 5,320,610, and a continuation-in-part of Ser. No. 868,578, Apr. 15, 1992, Pat. No. 5,336,176.

[51] Int. Cl.⁵ ............................................. A61M 5/178
[52] U.S. Cl. .................................. 604/165; 606/185; 604/157
[58] Field of Search ................ 604/157, 158, 164, 165, 604/264, 274; 606/185

[56] References Cited

U.S. PATENT DOCUMENTS

| | | |
|---|---|---|
| Re. 32,922 | 5/1989 | Levin et al. |
| 1,527,291 | 2/1925 | Zorraquin |
| 2,496,111 | 1/1950 | Turkel |
| 2,623,521 | 12/1952 | Shaw |
| 2,630,803 | 3/1953 | Baran |
| 4,254,762 | 3/1981 | Yoon |
| 4,345,589 | 8/1982 | Hiltebrandt |
| 4,442,836 | 4/1984 | Meinecke et al. |
| 4,488,545 | 12/1984 | Shen |
| 4,503,856 | 3/1985 | Cornell et al. |
| 4,535,773 | 8/1985 | Yoon |
| 4,559,041 | 12/1985 | Razi |
| 4,601,710 | 7/1986 | Moll |
| 4,627,841 | 12/1986 | Dorr |
| 4,654,030 | 3/1987 | Moll et al. |
| 4,670,008 | 6/1987 | Von Albertini |
| 4,677,979 | 7/1987 | Burns |
| 4,747,831 | 5/1988 | Kulli |
| 4,817,603 | 4/1989 | Turner et al. |
| 4,820,275 | 4/1989 | Haber et al. |
| 4,869,717 | 9/1989 | Adair |
| 4,889,117 | 12/1989 | Stevens |

(List continued on next page.)

FOREIGN PATENT DOCUMENTS

| | | |
|---|---|---|
| 2544262 | 4/1977 | Germany |
| 1435246 | 11/1988 | U.S.S.R. |

*Primary Examiner*—Paul Prebilic

[57] ABSTRACT

An automatic retractable safety penetrating instrument includes a sleeve for being introduced in a body cavity and a penetrating member disposed within the sleeve and having a sharp distal tip for penetrating a wall of the cavity. A retracting mechanism biases the penetrating member to a retracted position wherein the sharp distal tip is in a safe, protected position, and the penetrating member is movable distally from the retracted position to an extended position wherein the sharp distal tip extends beyond a distal end of the sleeve. The penetrating member is automatically locked against movement to the retracted position upon axial rotation of a locking and releasing mechanism in response to movement of the penetrating member to the extended position. An operating member is biased to move distally upon the sleeve distal end entering the body cavity such that the locking and releasing mechanism is axially rotated in response to distal movement of the operating member. Rotation of the locking and releasing mechanism upon the sleeve distal end entering the body cavity causes the penetrating member to be released for movement to the retracted position. Upon release of the penetrating member, the retracting mechanism automatically moves the penetrating member to the retracted position with the sharp distal tip in the safe, protected position. A method of establishing communication with an anatomical cavity utilizing an automatic retractable safety penetrating instrument including a sleeve and a penetrating member disposed in the sleeve includes the steps of forcing the automatic retractable safety penetrating instrument through tissue to enter the anatomical cavity and rotating a mechanism of the instrument about a longitudinal axis of the penetrating member to unlock the penetrating member causing movement of the penetrating member to a retracted position in response to entry of the automatic retractable safety penetrating instrument into the anatomical cavity.

39 Claims, 15 Drawing Sheets

U.S. PATENT DOCUMENTS

| | | |
|---|---|---|
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1992 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. ............ 604/165 |
| 5,152,754 | 10/1992 | Plyley et al. . |
| 5,158,552 | 10/1992 | Borgia et al. . |
| 5,207,647 | 5/1993 | Phelps . |
| 5,226,426 | 7/1993 | Yoon ....................... 606/185 |

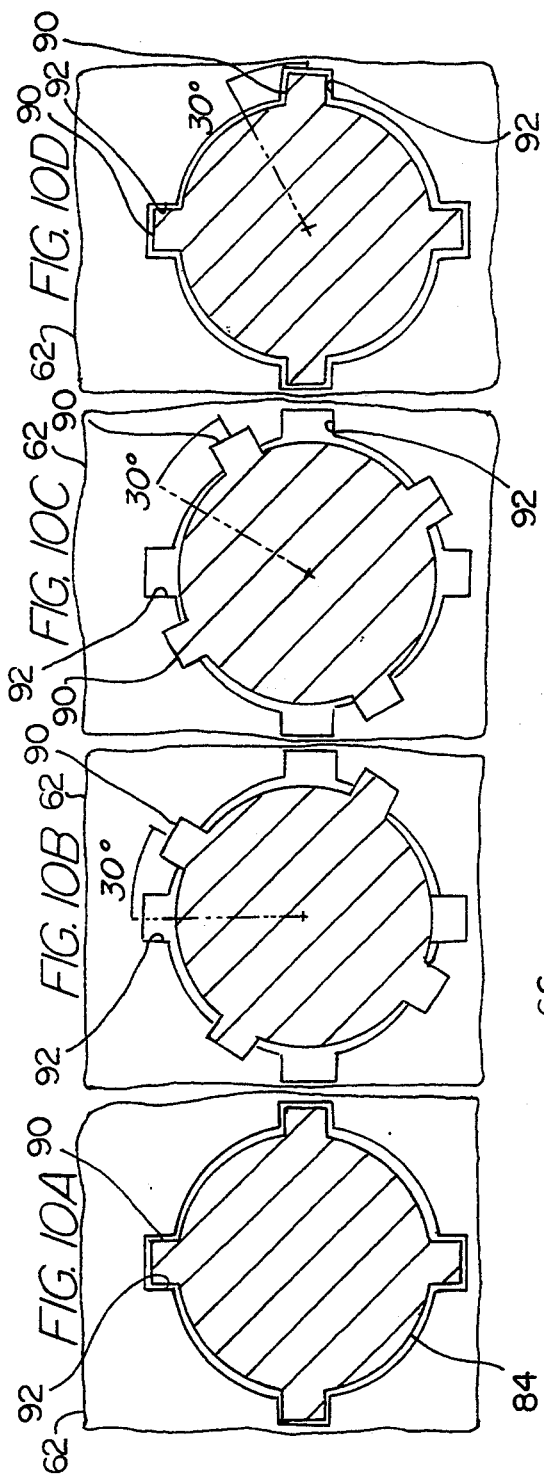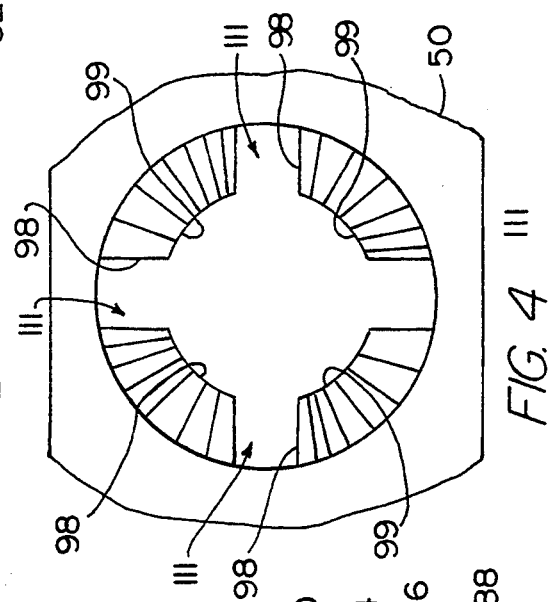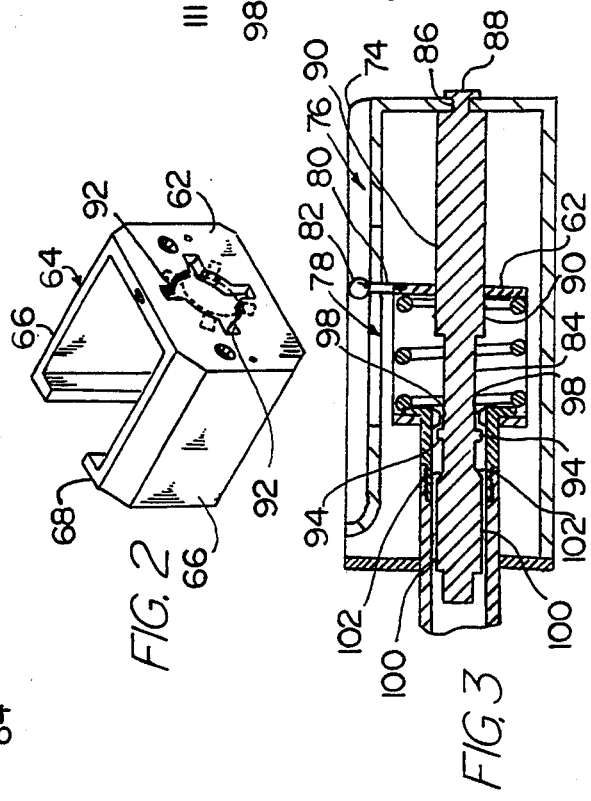

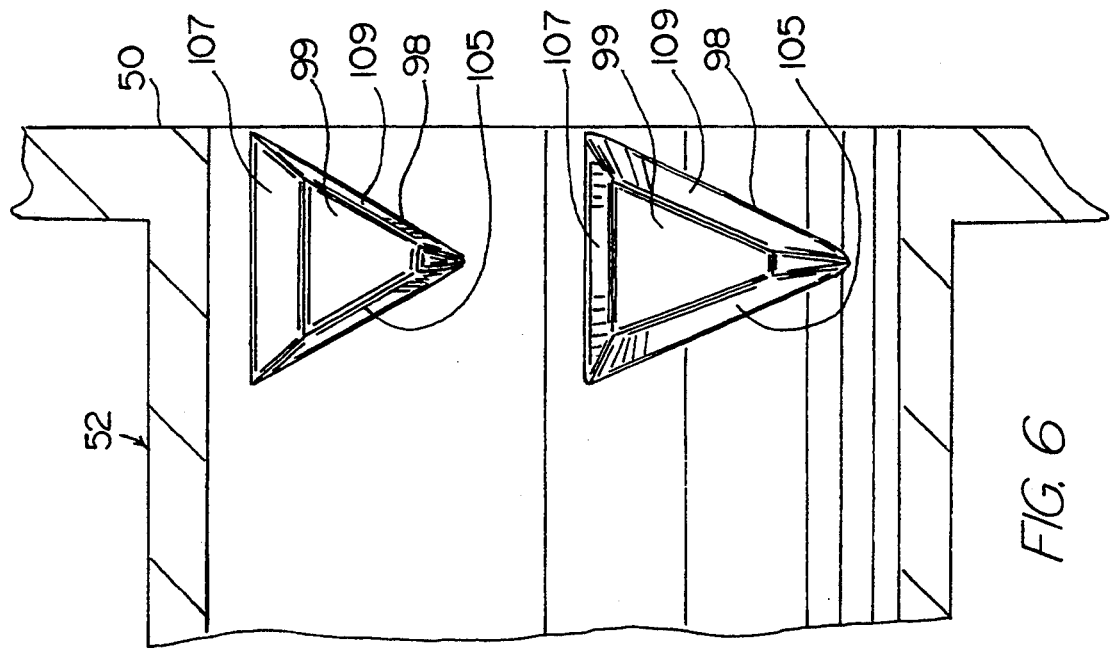
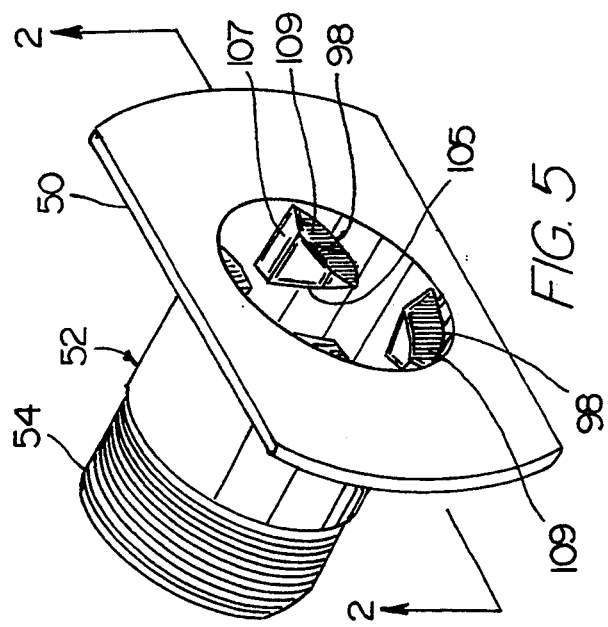

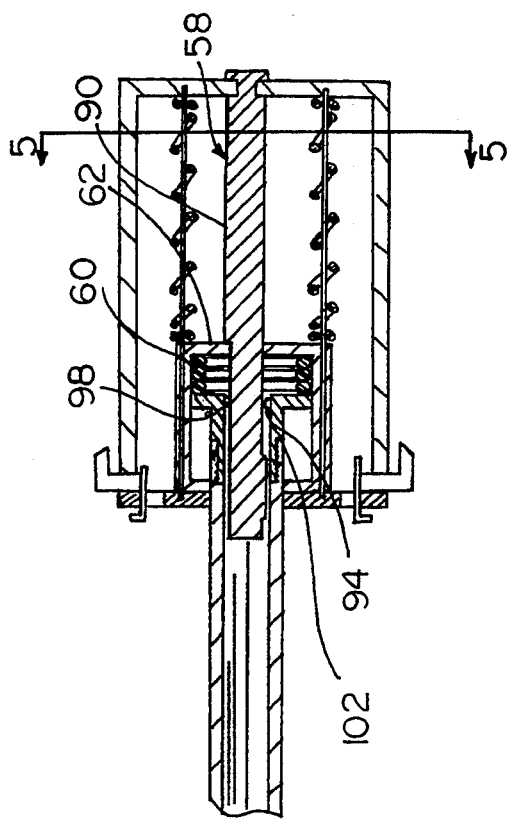
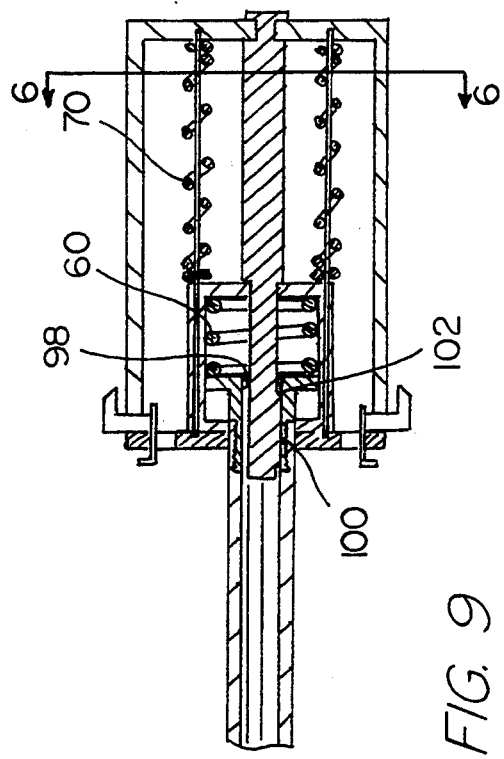
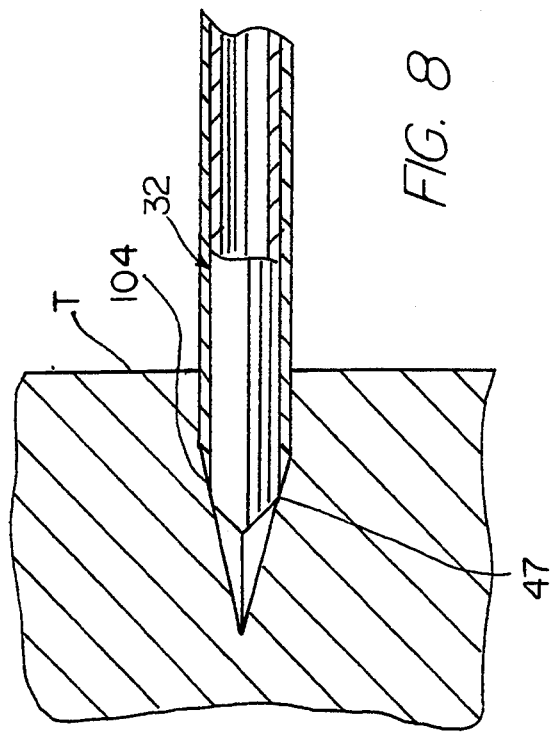
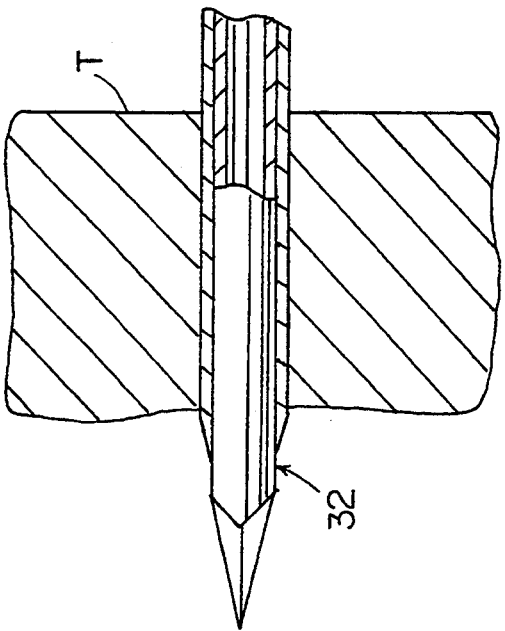
FIG. 8
FIG. 9

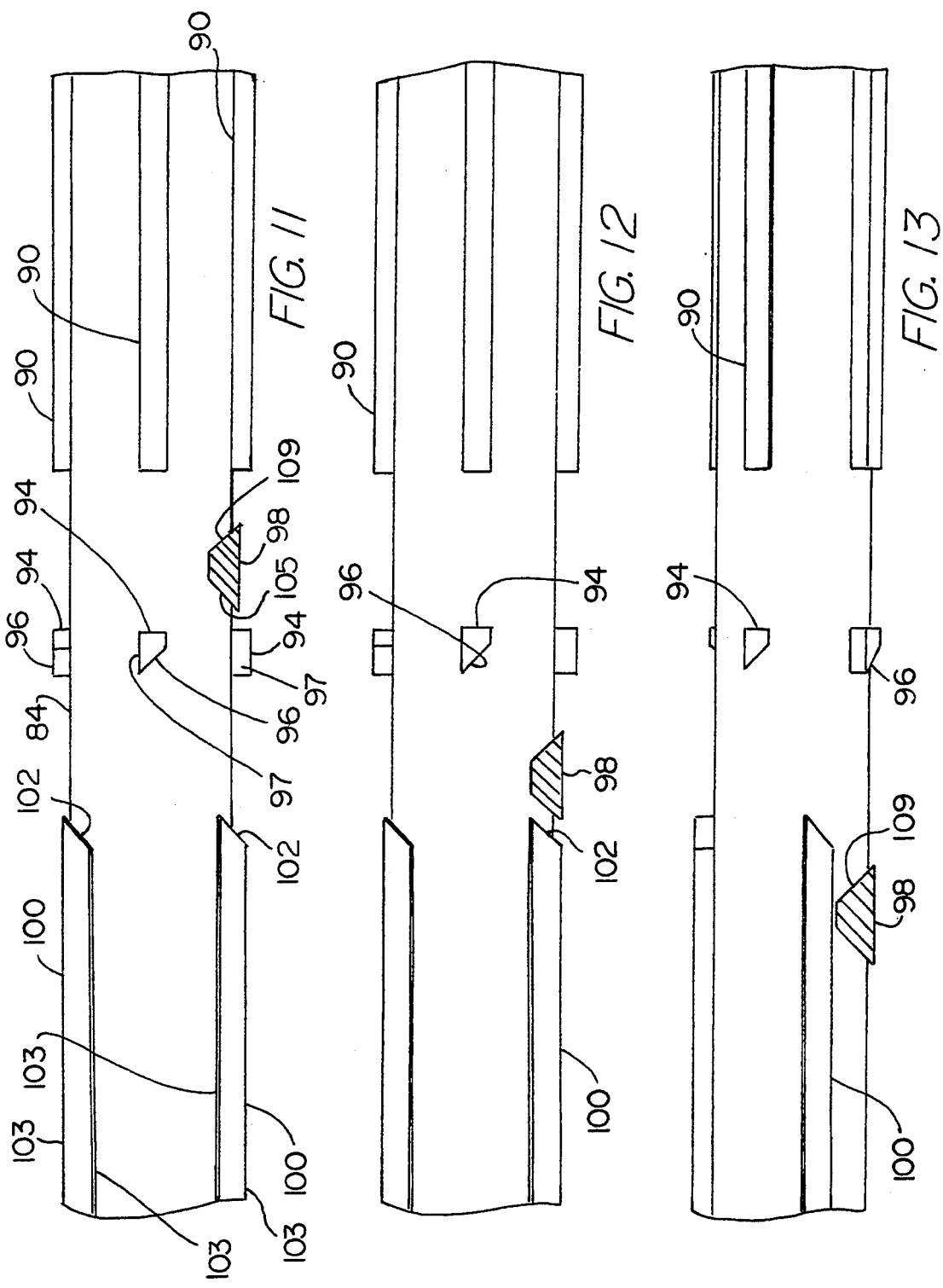

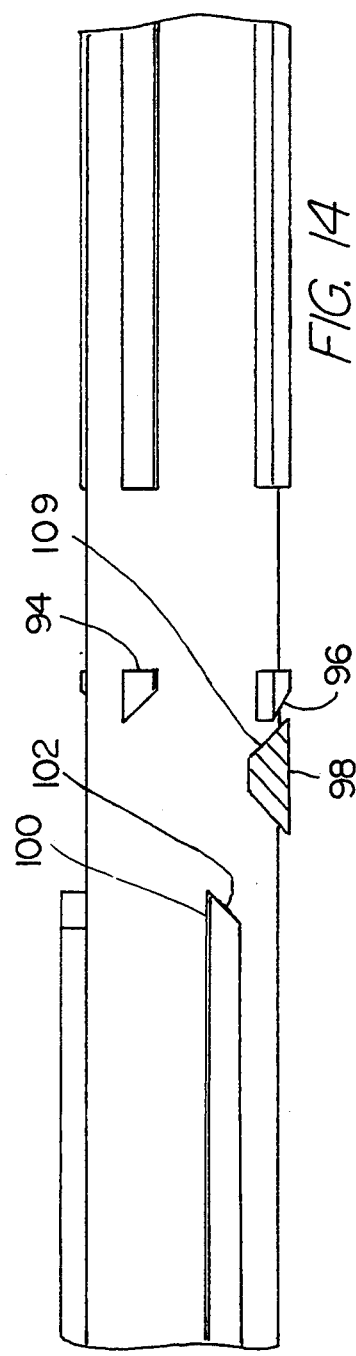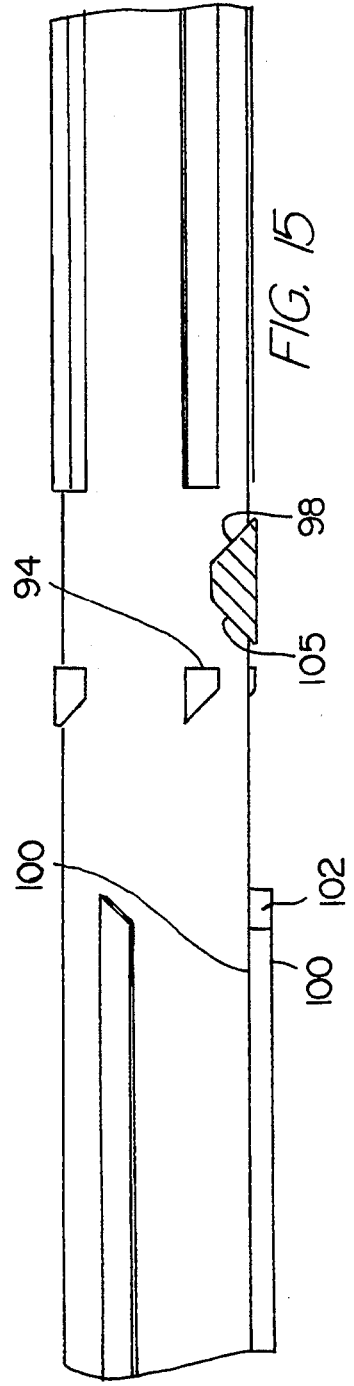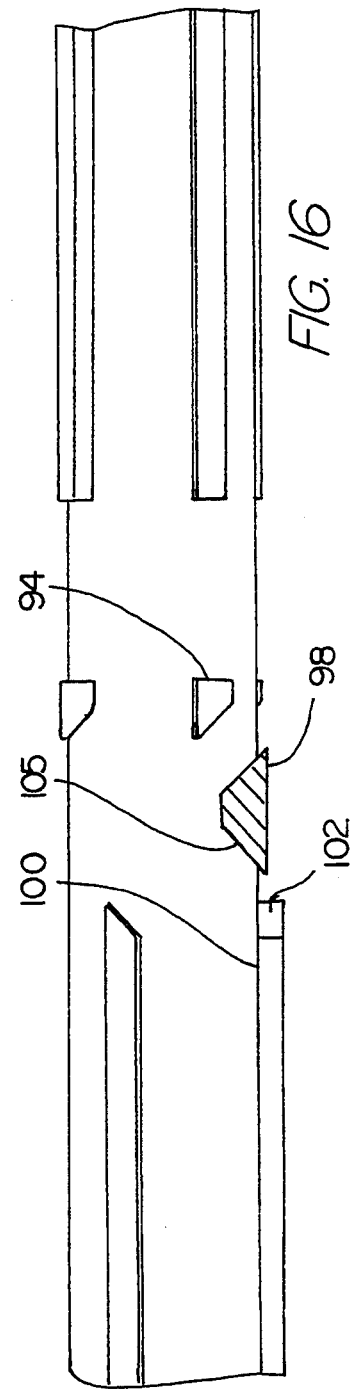

AUTOMATIC RETRACTABLE SAFETY PENETRATING INSTRUMENT

CROSS-REFERENCES TO RELATED APPLICATIONS

This application is a continuation-in-part of pending patent applications Ser. No. 07/800,507, filed Nov. 27, 1991, Ser. No. 07/805,506 filed Dec. 6, 1991, Ser. No. 07/808,325, filed Dec. 16, 1991 now U.S. Pat. No. 5,324,260, Ser. No. 07/848,838, filed Mar. 10, 1992 and Ser. No. 07/868,566 now U.S. Pat. No. 5,320,610 and Ser. No. 07/868,578, both filed Apr. 15, 1992 now U.S. Pat. No. 5,336,176. The specifications of the above patent applications are incorporated herein by reference.

BACKGROUND OF THE INVENTION

1. Field of the Invention

The present invention pertains to safety penetrating instruments and, more particularly, to automatic retractable safety penetrating instruments having sleeves for introduction into anatomical cavities and penetrating members with sharp tips disposed within the sleeves for penetrating cavity walls with automatic retraction of the penetrating members into the sleeves upon penetration to protect tissue and organ structures within the cavities from the sharp tips of the penetrating members.

2. Discussion of the Prior Art

Penetrating instruments are widely used in medical procedures to gain access to anatomical cavities ranging in size from the abdomen to small blood vessels, such as veins and arteries, epidural, plural and subachroniad spaces, heart ventricles and spinal and synovial cavities, with access being established via a sleeve positioned during penetration into the cavity with the penetrating instrument. Use of penetrating instruments has become an extremely popular and important first step in endoscopic, or least invasive, surgical procedures to establish an endoscopic portal for many various procedures with access being established via portal sleeves of the penetrating instruments. Such penetrating instruments typically include a portal sleeve and a penetrating member disposed within the portal sleeve and having a sharp tip or point to pierce or penetrate the tissue forming the cavity wall with the force required to penetrate the cavity wall being dependent upon the type and thickness of the tissue of the wall. Once the wall is penetrated, it is desirable to prevent the sharp tip of the penetrating member from inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety trocars having a spring-biased protective shield disposed between an outer sleeve and an inner trocar are marketed by Ethicon, Inc. as the Endopath and by United States Surgical Corp. as the Surgiport. U.S. Pat. Nos. 4,535,773 to Yoon, U.S. Pat. No. 4,601,710 to Moll and U.S. Pat. No. 4,654,030 to Moll et al are illustrative of such safety trocars. A trocar disposed within a portal sleeve and retractable within the sleeve when force from tissue contact is removed from the sharp tip of the trocar is set forth in U.S. Pat. No. 4,535,773 to Yoon.

SUMMARY OF THE INVENTION

It is a primary object of the present invention to provide improved, simplified automatic retractable safety penetrating instruments capable of use in a wide variety of procedures and having the general configuration and appearance of standard penetrating instruments.

Another object of the present invention is to provide an automatic retractable safety penetrating instrument with simplified structure allowing the instrument to be economically manufactured to be reusable or disposable for single patient use.

A further object of the present invention is to provide an automatic retractable safety penetrating instrument having a locking and releasing mechanism rotatable around an axis aligned with a longitudinal axis of the automatic retractable safety penetrating instrument for automatically releasing a retracting mechanism to permit retraction of a penetrating member upon entry of the instrument into an anatomical cavity.

An additional object of the present invention is to position a rotatable locking and releasing mechanism within a shaft of a penetrating member of an automatic retractable safety penetrating instrument to reduce the size of the proximal hub or handle for the penetrating member.

A further object of the present invention is to form a penetrating member of an automatic retractable safety penetrating instrument of telescoping parts such that the distal end can be moved proximally relative to the shaft upon retraction to reduce the length of the proximal hub or handle.

Yet another object of the present invention is to provide an automatic retractable safety penetrating instrument with a locking and releasing mechanism that is automatically, incrementally rotated in a predetermined direction in response to movement of the automatic retractable safety penetrating instrument from a retracted position to an extended position, from the extended position to an operative position and from the operative position toward the extended position during operation of the automatic retractable safety penetrating instrument.

A further object of the present invention is to provide a cam mechanism for axially rotating a locking and releasing mechanism of an automatic retractable safety penetrating instrument in response to penetration into a body cavity by the automatic retractable safety penetrating instrument.

It is also an object of the present invention to provide a retracting mechanism including a bias device for biasing a penetrating member of an automatic retractable safety penetrating instrument to a retracted position and a locking and releasing mechanism to a rotated position releasing the penetrating member for movement to the retracted position in response to the automatic retractable safety penetrating instrument entering a body cavity.

Another object of the present invention is to provide a method of establishing communication with an anatomical cavity utilizing an automatic retractable safety penetrating instrument including the step of rotating a mechanism about a longitudinal axis of the penetrating member to unlock the penetrating member causing movement of the penetrating member to a retracted position in response to entry of the automatic retractable safety penetrating instrument into an anatomical cavity.

Some of the advantages of the present invention over the prior art are that the automatic retractable safety penetrating instrument can be provided and stored in a rest state with the sharp distal tip withdrawn into the portal sleeve in a safe, protected position and with the bias devices in relaxed states, small or narrow anatomical cavities can be safety penetrated, sleeves can safely be introduced into anatomical cavities of various sizes to expand the use of least invasive procedures in many areas including, for example, cardiac, brain, vascular, chest, genitourinary system, breast and spinal fields, safe penetration of cavities can be accomplished with no parts of the safety penetrating instrument other than the sleeve protruding beyond the sharp tip of the penetrating member as is particularly desirable where organ structures adhere to cavity walls, the automatic retractable safety penetrating instrument encourages the use of a smooth, continuous penetration motion by the surgeon thereby reducing trauma, tears and irregular surfaces in the tissue of the cavity wall, the automatic retractable safety penetrating instrument can be used to penetrate anatomical cavities of the type containing organ structures that could be injured by contact with even a blunt instrument part such as a safety shield, the automatic retractable safety penetrating instrument can be economically made of plastic with relatively few components, safe penetration is achieved while permitting injection or evacuation of fluids, a single puncture can be used for both insufflation and forming an endoscopic portal thereby simplifying diagnostic and surgical procedures, trauma and damage to tissue is minimized, tissue jamming and trapping are avoided and automatic retractable safety penetrating instruments according to the present invention can be inexpensively manufactured to be reusable or disposable for universal use.

The present invention is generally characterized in an automatic retractable safety penetrating instrument including a sleeve for being introduced through a wall of a body cavity to provide communication therewith and a penetrating member disposed within the sleeve and having a sharp distal tip for penetrating the cavity wall. A retracting mechanism engages a proximal end of the penetrating member and biases the penetrating member to a retracted position with the sharp distal tip in a safe, protected position. The penetrating member is manually movable in a distal direction from the retracted position to an extended position wherein a junction proximally joining the sharp distal tip to a body of the penetrating member is disposed beyond a distal end of the sleeve. Movement of the penetrating member to the extended position causes axial rotation of a locking and releasing mechanism such that the penetrating member is prevented from moving to the retracted position due to a retracting member of the retracting mechanism being locked in place upon rotation of the locking and releasing mechanism. The penetrating member is biased distally to move in a proximal direction to an operative position wherein the junction is aligned with the distal end of the sleeve during penetration of the cavity wall and to move distally toward the extended position upon the sleeve distal end entering the body cavity. Distal movement of the penetrating member toward the extended position causes the locking and releasing mechanism to be axially rotated, and rotation of the locking and releasing mechanism causes the retracting member to be automatically released such that the penetrating member is automatically moved to the retracted position with the sharp distal tip in a safe, protected position. A method of establishing communication with an anatomical cavity utilizing an automatic retractable safety penetrating instrument including a penetrating member and a sleeve disposed around the penetrating member is characterized in the steps of forcing the automatic retractable safety penetrating instrument through tissue to enter a body cavity and rotating a mechanism of the automatic retractable safety penetrating instrument about a longitudinal axis of the penetrating member to unlock the penetrating member causing movement of the penetrating member to a retracted position with a sharp distal tip of the penetrating member in a safe, protected position in response to entry of the automatic retractable safety penetrating instrument into the body cavity.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 2 is a perspective view of the retracting member of the automatic retractable safety penetrating instrument of FIG. 1.

FIG. 3 is a broken side view, partly in longitudinal section, of the hub of the automatic retractable safety penetrating instrument of FIG. 1.

FIG. 4 is a broken, proximal end view of the penetrating member of the automatic retractable safety penetrating instrument of FIG. 1.

FIG. 5 is a perspective view of the proximal end of the penetrating member of FIG. 4.

FIG. 6 is a sectional view taken along line 2—2 of FIG. 5.

FIG. 8 is a broken side view, partly in longitudinal section, of the automatic retractable safety penetrating instrument of FIG. 1 in an operative position during penetration of tissue.

FIG. 9 is a broken side view, partly in longitudinal section, of the automatic retractable safety penetrating instrument of FIG. 1 upon penetration through the tissue.

FIG. 10A is a broken view, partly in section, of the locking and releasing mechanism and the retraction plate taken along line 3—3 of FIG. 1.

FIG. 10B is a broken view, partly in section, of the locking and releasing mechanism and the retraction plate taken along line 4—4 of FIG. 7.

FIG. 10C is a broken view, partly in section, of the locking and releasing mechanism and the retraction plate taken along line 5—5 of FIG. 8.

FIG. 10D is a broken view, partly in section, of the locking and releasing mechanism and the retraction plate taken along line 6—6 of FIG. 9.

FIGS. 11-16 are broken side views, partly in longitudinal section, of the locking and releasing mechanism and the cam mechanism for the automatic retractable safety penetrating instrument of FIG. 1 showing the relative positions of the locking and releasing mechanism and the cam mechanism during operation of the instrument.

FIG. 17 is a broken side view, partly in longitudinal section, of a modification of the automatic retractable safety penetrating instrument according to the present invention in the rest state.

DESCRIPTION OF THE PREFERRED EMBODIMENTS

Figure 1:
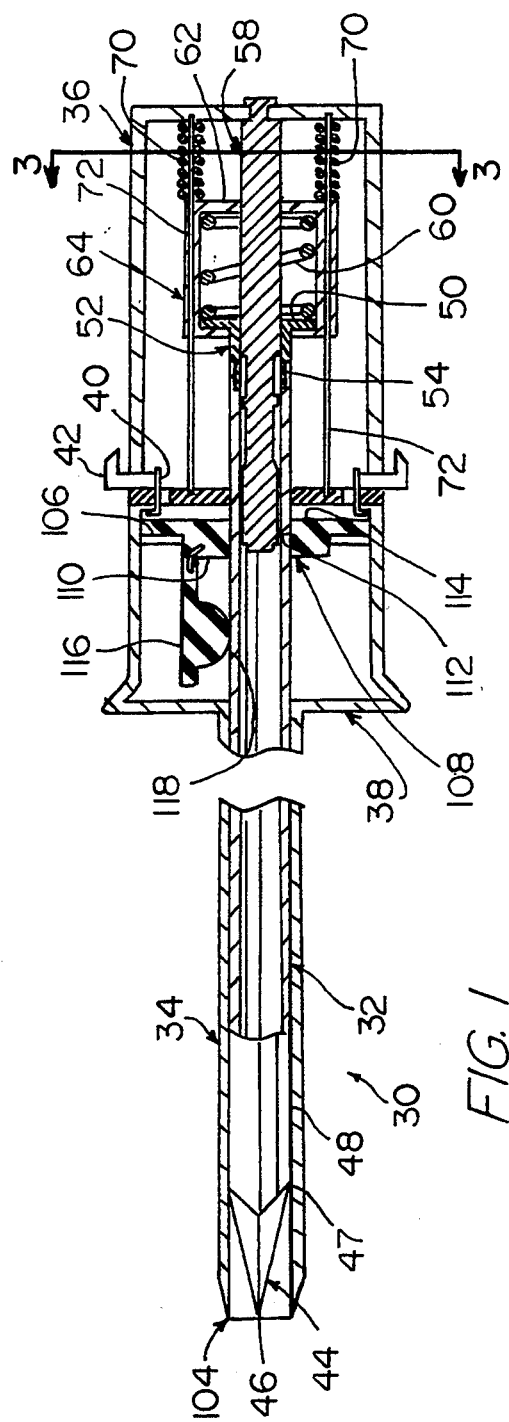
FIG. 1 is a broken side view, partly in longitudinal section, of an automatic retractable safety penetrating instrument according to the present invention in a rest state.

An automatic retractable safety penetrating instrument 30 according to the present invention is illustrated in FIG. 1 and includes an elongate penetrating member 32, an outer sleeve, such as portal sleeve 34, concentrically disposed around the penetrating member, a hub 36 mounting penetrating member 32 and a valve housing 38 mounting portal sleeve 34. The hub 36 can be latched to housing 38 with the use of any suitable releasable mechanism, such as detents 40 operated by buttons 42, allowing the hub to be removed from the housing withdrawing the penetrating member from the portal sleeve. Accordingly, the automatic retractable safety penetrating instrument 30 can be considered to be formed of a portal unit and a penetrating unit, the portal unit including portal sleeve 34 and housing 38 and the penetrating unit including penetrating member 32 and hub 36.

Penetrating member 32 is preferably made of a medical grade material, such as stainless steel, and has an outer diameter or size dependent upon the surgical procedure to be performed and the anatomical cavity to be penetrated. The penetrating member 32 has a distal end 44 terminating at a sharp tip 46 for penetrating anatomical tissue. The distal end 44 can have various solid or hollow geometric configurations including various trocar and needle distal end configurations; and, as shown in FIG. 1, the distal end is formed as a trocar with equally spaced end surfaces or facets tapering distally to sharp tip 46 and terminating proximally at junction 47 joining the facets to an elongate body 48 which can be cylindrical or have any desired configuration in cross-section. Body 48 extends proximally from junction 47 to terminate at an end flange 50 at a proximal end 52 of the penetrating member, the proximal end being disposed in hub 36 with body 48 passing through an aperture in a front wall of the hub. The proximal end 52 can be formed integrally, unitarily with body 48, or the proximal end can be formed separate from body 48 and secured thereto in any suitable manner, such as with threads 54, to simplify assembly of the automatic retractable safety penetrating instrument and to allow the body 48 to be removed and replaced on proximal end 52 for disposability or single patient use. The body 48 can be hollow or tubular along the length of the penetrating member, and an aperture (not shown) can be disposed at the distal end 44 to allow communication entirely through the instrument 30 via a valve (not shown) carried on the rear wall of hub 36, or the body can be partly hollow or tubular to receive a locking and releasing mechanism 58 extending distally from the rear wall of the hub and into the proximal end of the penetrating member. A coiled helical operating spring 60 is connected between end flange 50 and a retraction plate 62 of a retracting member 64, the plate having an opening allowing passage therethrough of the locking and releasing mechanism 58 with the operating spring disposed concentrically around the locking and releasing mechanism. As shown in FIGS. 1 and 2, retracting member 64 includes opposing side walls 66 extending longitudinally, distally from retraction plate 62 to a transverse forward wall 68 of the retracting member to define an enclosure or box-like structure disposed within the hub for receiving the operating spring 60 and end flange 50 with the proximal end of the penetrating member passing through a slot or opening in forward wall 68. A retracting mechanism engages the proximal end of the penetrating member and includes retracting member 64 and a bias device including a pair of coiled helical retracting springs 70 connected between retraction plate 62 and the rear wall of the hub. If required, guide rods 72 can extend from the rear wall of the hub to the front wall thereof to provide a guide to maintain the retracting springs 70 in axial alignment, the guide rods passing through retracting member 64. The retracting member can be made integrally, unitarily as one piece or as separate pieces, and the retracting mechanism can be formed integrally, unitarily depending upon the bias device, springs 70 in the embodiment of FIG. 1, utilized. The retracting member can have various cylindrical or non-cylindrical configurations to mount the end flange and be moved by the bias device, retracting springs 70 in FIG. 1.

Hub 36 can be made of any suitable material to be disposable or reusable and has an external configuration to cooperate with housing 38 to facilitate grasping with one hand for use in penetrating tissue. Hub 36 can have any desired configuration in cross-section and is shown in FIG. 1 as being substantially rectangular. The hub has a longitudinal slot for receiving a pin secured to retracting member 64. The pin and slot are not shown in FIG. 1 for the sake of simplicity and are illustrated in FIG. 3. As illustrated in FIG. 3, a top wall 74 of the hub has a central recessed channel 76 aligned with a longitudinal axis of the automatic retractable safety penetrating instrument, and a slot 78 is disposed in the channel 76 in alignment with the instrument longitudinal axis. A pin 80 is threadedly secured in the periphery of retracting member 64, the pin being shown in FIG. 3 secured in the periphery of the retraction plate 62. Pin 80 extends through slot 78 and has a "T" configuration to terminate at an external knob 82.

The locking and releasing mechanism 58, which actuates the retracting mechanism, is best illustrated in FIG. 3 and includes a shaft 84 that can be solid or hollow with a cylindrical or any other desired configuration in cross-section. Shaft 84 has a longitudinal axis coaxially aligned with the longitudinal axis of the automatic retractable safety penetrating instrument and is proximally joined to a neck 86 mounted in the rear wall of the hub, the neck terminating proximally at a cap, knob or flange 88. The hub rear wall is held between the shaft and the cap such that axial movement of the locking and releasing mechanism is prevented while rotational movement of the locking and releasing mechanism around the shaft longitudinal axis is permitted. Locking members including a plurality of keys 90 are disposed along the periphery of shaft 84 at 90° spaced locations, the keys extending longitudinally, distally from a proximal end of the shaft parallel with the longitudinal axis of the automatic retractable safety penetrating instrument. A plurality of keyways or slots 92, best illustrated in FIG. 2, corresponding in configuration to the keys 90 are formed in retraction plate 62 at 90° spaced locations along the opening receiving shaft 84 such that the retraction plate 62 can be moved longitudinally along the locking and releasing mechanism when the keys are within or aligned with the keyways. As shown in FIGS. 3 and 11, a plurality of projections 94 are disposed along the periphery of shaft 84 spaced distally from and longitudinally aligned with the keys 90. Projections 94 have contact sides or surfaces 96 to be engaged or contacted by operating members or cams 98 on the penetrating member to cause rotation of the locking and releasing mechanism around the shaft longitudinal axis when the penetrating member is moved in a proximal direction relative to the locking and releasing mechanism during penetration of tissue as will be explained further below. Projections 94 can have a triangular configuration, a quadrilateral configuration as shown in FIG. 12 or any other desired configuration with sides, surfaces or portions thereof to be engaged by the cams to produce rotation of the locking and releasing mechanism. In the instrument 30, sides 96 are acutely angled in a proximal direction from sides 97 of the projections disposed parallel with the instrument longitudinal axis as illustrated in FIG. 11. A plurality of raised ribs 100 are disposed along the periphery of shaft 84 at 90° spaced locations distally spaced from and angularly offset 45° from the projections 94, the ribs extending longitudinally along the shaft parallel with the longitudinal axis of the instrument as illustrated in FIGS. 3 and 11. Ribs 100 have contact surfaces or sides 102 at proximal ends thereof for being engaged or contacted by the cams 98 to cause rotation of the locking and releasing mechanism when the penetrating member is moved in a distal direction during operation of the instrument as will be explained further below. In the instrument 30, the sides 102 are acutely angled in a distal direction from sides 103 of the ribs disposed parallel with the instrument axis as shown in FIG. 11. As shown in FIGS. 4–6, cams 98 project inwardly from an inner diameter surface of the wall of the penetrating member proximal end at 90° spaced locations to be carried by the penetrating member along shaft 84. The cams can have an angular, wedge, multi-sided or curved shape or any other shape to engage the projections and the ribs to cam or rotate the locking and releasing mechanism in response to longitudinal movement of the penetrating member as will be explained further below. As shown, the cams have a truncated pyramidal configuration with arcuate end surfaces 99 for being moved along the circumference of shaft 84, the cams being aligned with each other in a circumferential direction and separated by gaps or spaces 111 sufficiently large in size to allow passage thereby of keys 90, projections 94 and ribs 100. Sides or surfaces 105 of the cams are acutely angled in a proximal direction from sides 107 of the cams disposed parallel with the instrument longitudinal axis to engage surfaces 102 of ribs 100 to rotate the locking and releasing mechanism, and sides 109 of the cams are acutely angled in a distal direction from sides 107 to engage surfaces 96 of projections 94 to rotate the locking and releasing mechanism as will be explained further below. As previously noted, a valve, which can be of any conventional design, can be provided along the rear wall of the hub such as in flange 88, and the locking and releasing mechanism can be formed hollow or with an internal passage along the length of the locking and releasing mechanism as illustrated at 185 in FIG. 18, the passage being aligned with the valve and the lumen of the penetrating member to allow passage of fluid entirely through the instrument for additional confirmation of cavity penetration via leakage detection and for introduction and aspiration of fluids through the instrument where the penetrating member is hollow along its length and provided with an aperture at the distal end establishing fluid communication through the instrument. The locking and releasing mechanism can be made as one piece or multiple pieces dependent upon the hub construction and the operating member, cams 98 in the embodiment of FIG. 1, utilized to actuate the retracting mechanism. As shown, the locking and releasing mechanism is unitarily, integrally formed of a single piece of material such as metal or plastic. If desired, a control tube such as control tube 187 illustrated in FIG. 18 can be disposed in the locking and releasing mechanism where shaft 84 is hollow or formed with an internal passage, and a valve, which can be of any conventional design, can be provided in communication with the lumen of the control tube to control fluid flow through the instrument.

Sleeve 34 can be a portal sleeve as shown, a cannula or any other tubular structure such as a catheter for intravenous use designed to establish communication with an anatomical cavity and is preferably made of a substantially cylindrical length of rigid or flexible and transparent or opaque material, such as stainless steel or other suitable, medically acceptable, plastic or metal material. The sleeve has an outer diameter dependent upon the size of the penetrating member and the surgical procedure to be performed, the sleeve typically ranging in size from portal sleeve size to intravenous tube size. As illustrated in FIG. 1, the portal sleeve 34 has a distal end 104 with a configuration to produce a smooth profile with the distal end 44 of the penetrating member when the instrument is in an operative position to penetrate tissue, a proximal end mounted in or formed with a front wall of valve housing 38 and a lumen extending between the distal and proximal ends. Housing 38 can be made of any suitable material to be disposable or reusable and has a configuration in cross-section corresponding to the cross-sectional configuration of hub 36 with a flared external profile facilitating grasping during use. A wall 106 extends inwardly from housing 38 at the rear end thereof at a position distally spaced from the rear end of the housing to produce a recess for receiving detents 40, the wall 106 having a central passage for receiving a valve assembly 108. Valve assembly 108 can have any conventional configuration to produce a closed or sealed condition upon removal of the penetrating unit. As shown in FIG. 1, valve assembly 108 is formed as a unitary, one-piece integral construction of rubber or soft plastic to facilitate sealing to prevent fluid flow through the instrument when the penetrating unit is removed. The valve assembly 108 is formed of a body 110 having a passage 112 therethrough and a proximal flange 114 extending outwardly therefrom to be received in the recess at the rear end of the housing 38. The body 110 has a peripheral configuration to fit snugly within the passage through wall 106, and a valve member 116 extends distally from body 110 and has a normally sealed position with a hemispherical bulging end 118 received in a valve seat formed at an end of passage 112 to produce a normally closed, sealed configuration. To provide assisted bias toward the sealed configuration, a spring member can be embedded within the valve assembly 108 to bias the valve member 116 toward the valve seat. While the face of the valve seat is illustrated as being transverse to the longitudinal axis of the automatic retractable safety penetrating instrument 30, the valve seat can be angularly oriented.

Figure 7:
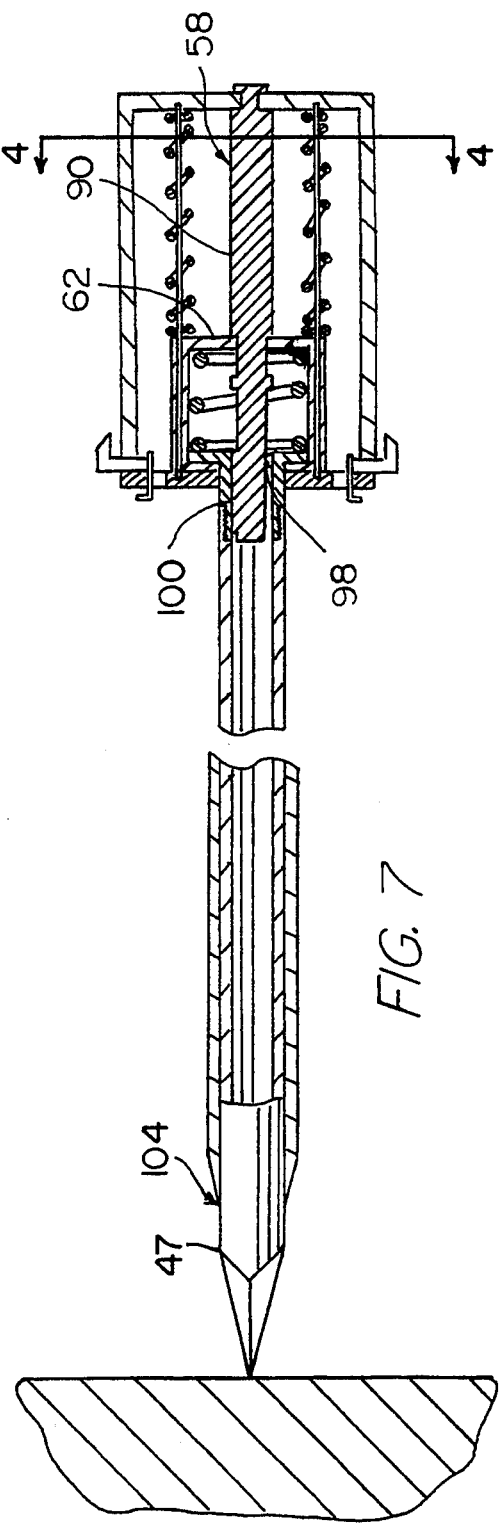
FIG. 7 is a broken side view, partly in longitudinal section, of the automatic retractable safety penetrating instrument of FIG. 1 in an extended position.

In use, the automatic retractable safety penetrating instrument 30 is normally provided in a rest state wherein the distal end 44 of penetrating member 32 is retracted within portal sleeve 34 to be in a safe, protected condition, the rest state coinciding with the retracted position for the penetrating member shown in FIG. 1. In the rest state, keys 90 are within keyways 92 of retraction plate 62, as shown in FIG. 10A, such that retraction plate 62 can be moved longitudinally along the locking and releasing mechanism, and the retracting springs 70 are in relaxed, unbiased or unloaded states causing retraction member 64 to be moved proximally, longitudinally along the locking and releasing mechanism carrying with it penetrating member 32 such that pin 80 is disposed at a proximal end of the slot 78. Operating spring 60 is similarly in an unbiased or relaxed state; and, accordingly, with the automatic retractable safety penetrating instrument initially provided in a rest state, no loading of the springs 60 and 70 exists such that the strength of the springs is not weakened and shelf life is increased. Cams 98 are disposed proximally of the projections 94 with sides 105 longitudinally aligned with surfaces 102 of ribs 100 and projections 94 longitudinally aligned with gaps 111, the positions of the cams and the locking and releasing mechanism in the rest state being shown in FIG. 11 wherein only a single cam is shown for simplification purposes. When it is desired to utilize the instrument 30 to penetrate tissue to introduce the portal sleeve into an anatomical cavity, the knob 82 is grasped and moved distally within slot 78 toward a distal end thereof causing retracting member 64 to move distally along the locking and releasing mechanism 58 due to the keys 90 being received in the keyways 92. The penetrating member 32 and, therefore, the cams 98, are moved distally by the retracting member, the cams moving distally past the projections 94 without contacting the surfaces 96 due to the projections 94 being aligned with gaps 111 as illustrated in FIG. 12. Once the retracting plate 62 is moved past distal ends of the keys 90 such that the keys are no longer within the keyways 92, sides 105 of cams 98 engage contact surfaces 102 of ribs 100 axially rotating or camming the locking and releasing mechanism in a clockwise direction around the shaft longitudinal axis a first angular or rotational increment of 30° as the ribs enter gaps 111 as seen when looking distally, i.e. to the left, in FIG. 13. Upon rotation of the locking and releasing mechanism 58, keys 90 will be angularly offset from keyways 92 as shown in FIG. 10B such that the retracting plate 62 will be held or locked in place against distal ends of the keys as shown in FIG. 7, with further distal movement of the retracting plate being prevented due to the knob 82 being disposed at the distal end of the slot 78. Locking of the retracting plate can be confirmed by feel and sound as the locking and releasing mechanism moves into place and also visually by viewing the position of knob 82 relative to slot 78. With the instrument 30 in the extended condition, sides 109 of cams 98 will be longitudinally aligned with surfaces 96 of projections 94 as shown in FIG. 13, and the distal end junction 47 of the penetrating member will be distally spaced from the distal end 104 of the portal sleeve by a distance that is the same as the distance that the cams 98 must be moved distally from the rest state to rotate the locking and releasing mechanism and lock the retracting plate against movement as shown in FIG. 7.

The instrument can now be utilized to penetrate tissue and enter an anatomical cavity. The hub and housing are grasped by a surgeon, and the instrument is forced against tissue T forming a wall of an anatomical cavity as shown in FIG. 8, causing penetrating member 32 to move proximally against the bias of operating spring 60 at which time the penetrating member will be in an operative position with the distal end junction 47 aligned with the distal end 104 of the portal sleeve to form a substantially smooth profile. As the penetrating member moves proximally during penetration of tissue T, cams 98 move proximally as shown in FIG. 14 causing sides 109 to engage surfaces 96 of projections 94 to axially rotate or cam the locking and releasing mechanism in a clockwise direction a second angular increment of 30° as the projections move into the gaps 111 as shown in FIG. 15. Upon rotation of the locking and releasing mechanism, the keys 90 remain angularly offset and not aligned with the keyways 92 such that retraction plate 62 remains held against the distal ends of the keys as shown in FIG. 10C, and sides 105 of cams 98 are again longitudinally aligned with surfaces 102 of ribs 100. Once the distal end of the instrument has passed through the tissue T as shown in FIG. 9, operating spring 60 will move penetrating member 32 distally causing distal movement of cams 98 as shown in FIG.

16 until sides 105 of cams 98 engage surfaces 102 of ribs 100 such that the locking and releasing mechanism 58 is again axially rotated clockwise a third angular increment of 30° to align keys 90 with keyways 92 and release the retracting mechanism as shown in FIG. 10D. Accordingly, retracting springs 70 will automatically move the retracting member 64 and with it the penetrating member 32 to a retracted position corresponding to the rest position shown in FIG. 1 with the sharp distal tip of the penetrating member within the portal sleeve in a safe protected position.

Once the distal end of the instrument has entered the anatomical cavity and the penetrating member has moved to the retracted position, the portal sleeve will have been introduced into the cavity such that the penetrating unit can be withdrawn from the portal unit. When the penetrating member is withdrawn, the valve member 116 will return to the biased position such that bulging end 118 will engage the valve seat to seal the portal unit from fluid flow therethrough from insufflation pressure. The one-piece construction of valve assembly 108 has the advantages of being inexpensive to manufacture by molding and of being easily replaceable when used with reusable portal units. Additionally, the axial length of passage 112 produces an elongate seal with penetrating member 32 minimizing escape of fluid during cavity penetration; and, if an instrument of a different size than the penetrating member is to be introduced after withdrawal of the penetrating unit, the valve assembly can be easily interchanged to install a valve assembly having a passage 112 of a diameter to seal along the different size instrument.

While coiled operating and retracting springs are shown in the instrument 30 with the retracting springs laterally offset from the longitudinal axis of the instrument and the operating spring concentric therewith and surrounding the locking and releasing mechanism, many different arrangements and types of springs or other bias devices including a magnetic bias can be utilized with the present invention. For example, the hub rear wall can be made of a magnetic material or one or more magnets can be mounted in the hub rear wall and the retraction plate can be made of a magnetizable material to be attracted to the hub rear wall. Although the instrument 30 is shown with cams 98 on the penetrating member and contact surfaces 96 and 102 on the locking and releasing mechanism, it will be appreciated that such parts can be reversed and that cams can be provided on the locking and releasing mechanism and contact surfaces provided on the penetrating member to cooperate with the cams to rotate the locking and releasing mechanism in response to movement of the penetrating member. Various other types of devices and mechanisms including springs mounted in torsion can be utilized in addition to the cams and contact surfaces to produce rotation of the locking and releasing mechanism in response to movement of the operating member or some other portion of the instrument; and, where the instrument is supplied with a safety shield or probe, the probe or shield can function as the operating member to produce rotation of the locking and releasing mechanism during operation of the instrument. The cams and contact surfaces can have various structural configurations to cooperate to rotate the locking and releasing mechanism incrementally during operation of the instrument such that the retracting member is held against movement in the extended and operative positions and is released upon penetration through tissue. The increments that the locking and releasing mechanism is allowed to rotate can vary in accordance with the structural configuration of the operating members and the locking and releasing mechanism, and the first, second and third increments need not be equal. By varying the locations for the projections and the ribs, the distances that the penetrating member must be moved longitudinally in order to rotate the locking and releasing mechanism for each increment can be controlled. Accordingly, the penetrating member need be moved only small amounts distally to rotate the locking and releasing mechanism when setting the instrument in the extended condition, proximally to rotate the locking and releasing mechanism during penetration of tissue and distally to actuate retraction upon penetration through the tissue. Although a plurality of keys, projections, ribs and cams has been shown, it will be appreciated that one or more keys, projections, ribs and cams can be utilized in the automatic retractable safety penetrating instrument. The locking and releasing mechanism can be arranged in the instrument 30 in many ways including within or externally of the penetrating member or within the hub or housing; and, where disposed within the penetrating member, the locking and releasing mechanism can be mounted at any location along the length of the penetrating member including the penetrating member distal end to be disposed entirely or substantially entirely within the penetrating member.

Figure 17:
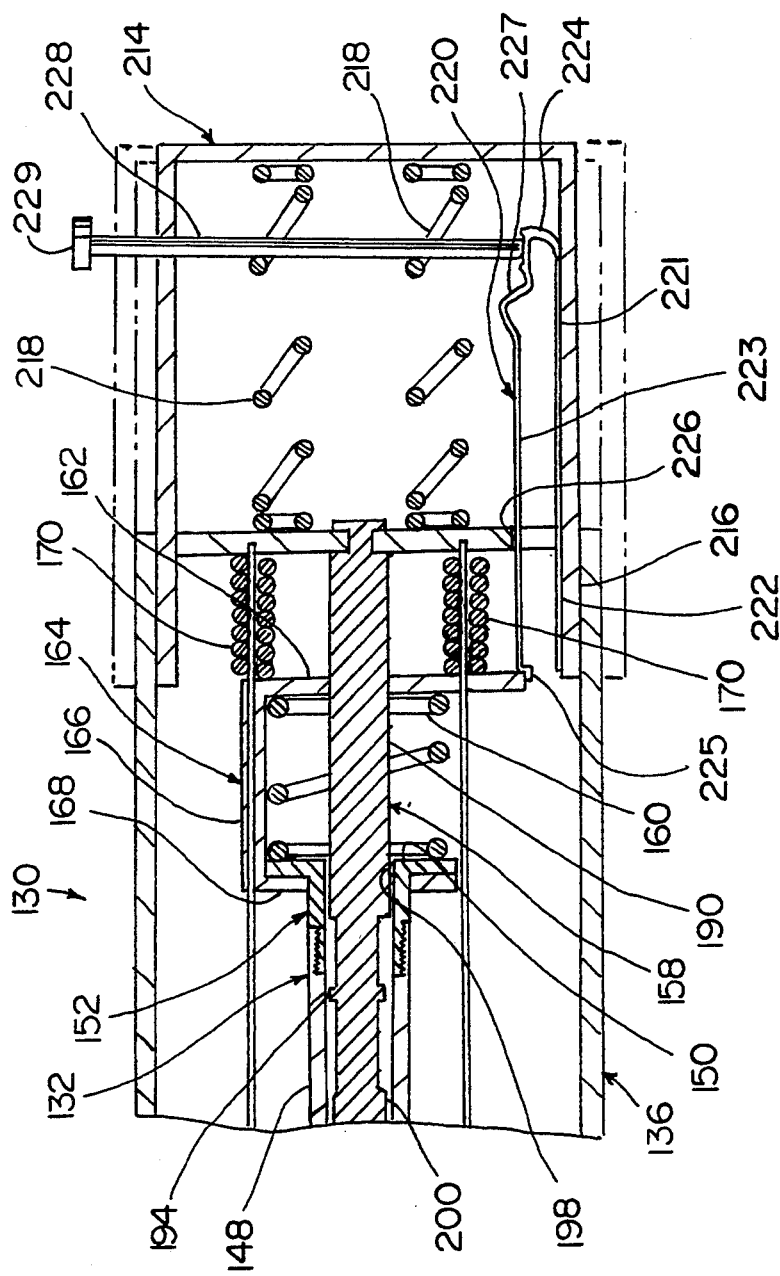

A modification of the automatic retractable safety penetrating instrument according to the present invention is illustrated at 130 in FIG. 17, only a portion of the penetrating unit of the instrument 130 being shown. The automatic retractable safety penetrating instrument 130 includes a portal unit as previously described and the penetrating unit including penetrating member 132 for being disposed within the portal sleeve of the portal unit and hub 136 mounting penetrating member 132. Penetrating member 132, only a proximal portion of which is shown in FIG. 17, is similar to penetrating member 32 and includes a body 148 terminating distally at a sharp tip for penetrating anatomical tissue and proximally at an end flange 150 at a proximal end 152 of the penetrating member, the proximal end being disposed in hub 136 with the body 148 passing through an aperture in a front wall (not shown) of the hub. Operating spring 160 is connected between end flange 150 and retraction plate 162 of retracting member 164 to bias the penetrating member in a distal direction, the plate having an opening allowing passage therethrough of the locking and releasing mechanism 158 extending distally from a rear wall of the hub into the proximal end of the penetrating member. Retracting member 164 includes a side wall 166 extending distally from plate 162 to a forward wall 168 to form a recess for receiving the operating spring 160 and end flange 150 with the proximal end of the penetrating member passing through an opening in the forward wall 168. Retracting springs 170 are connected between retraction plate 162 and a rear wall of hub 136 to bias the retracting member in a proximal direction. Locking and releasing mechanism 158 is similar to locking and releasing mechanism 58 and includes keys 190 for being received in keyways in retraction plate 162, projections 194 and ribs 200 for cooperating with cams 198 on the penetrating member to rotate the locking and releasing mechanism. An end cap 214 having an external configuration corresponding to the configuration of hub 136 has a skirt 216 disposed in hub 136 via a recess in the end wall of the hub. A bias device including a pair of helical coil mounting springs 218 is connected between the hub rear wall and a rear wall of end cap 214. If desired, guide rods can extend from the rear wall of the end cap and through the rear wall of the hub with the springs 218 disposed around the guide rods to maintain axial alignment of the springs 218. When the shaft 184 of the locking and releasing mechanism 158 is hollow as shown in dotted lines at 185 in FIG. 18, a control tube 187 illustrated in dotted lines can be mounted in the rear wall 215 of the end cap 214 to extend distally therefrom and into the lumen of shaft 184, and the control tube can be rotatably mounted. A valve, which can be of any conventional design, can be provided along the rear wall of the end cap, such as in alignment with the lumen of the control tube, to control fluid flow through the instrument 130. A push member 220 including a spring 221 is mounted in the end cap, the spring 221 including a base 222 secured to an inner surface of skirt 216 and terminating proximally at a bend 224, a push arm 223 joined to bend 224 and extending distally therefrom in the same direction as the base and a push finger 225 at a distal end of the push arm. The push arm 223 extends through a slot 226 in the rear wall of hub 136 and is biased in the direction of the instrument longitudinal axis such that the finger 225 is positioned to engage a portion of the retracting member, retraction plate 162 in FIG. 17, in the rest state for the instrument 130 shown in FIG. 17, the rest state corresponding to the retracted position for the penetrating member. A bump or cam 227 is provided on push arm 223 distally of bend 224, the bump protruding outwardly in the direction of the longitudinal axis of the instrument 130. A release mechanism including a release bar 228 extends through skirt 216 from a push button 229 disposed externally of the end cap, the release bar extending into the end cap laterally offset from control tube 187 in a direction transverse to the instrument axis to terminate at a tip engaged with bend 224.

Figure 18:
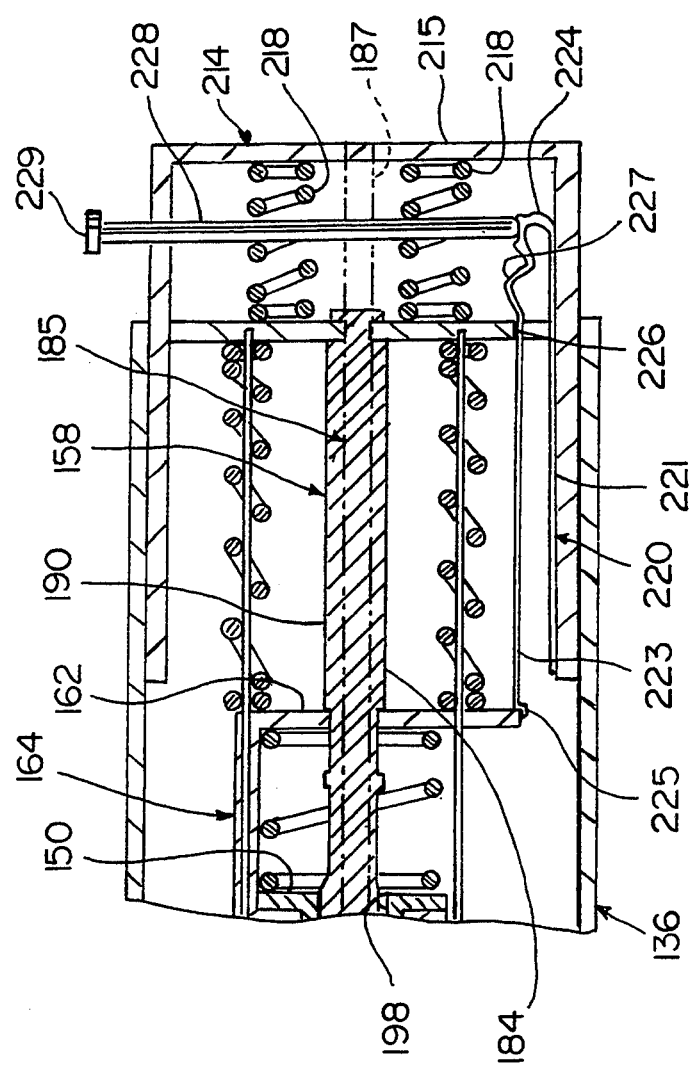
FIG. 18 is a broken side view, partly in longitudinal section, of the automatic retractable safety penetrating instrument of FIG. 17 in the extended position.
Figure 19:
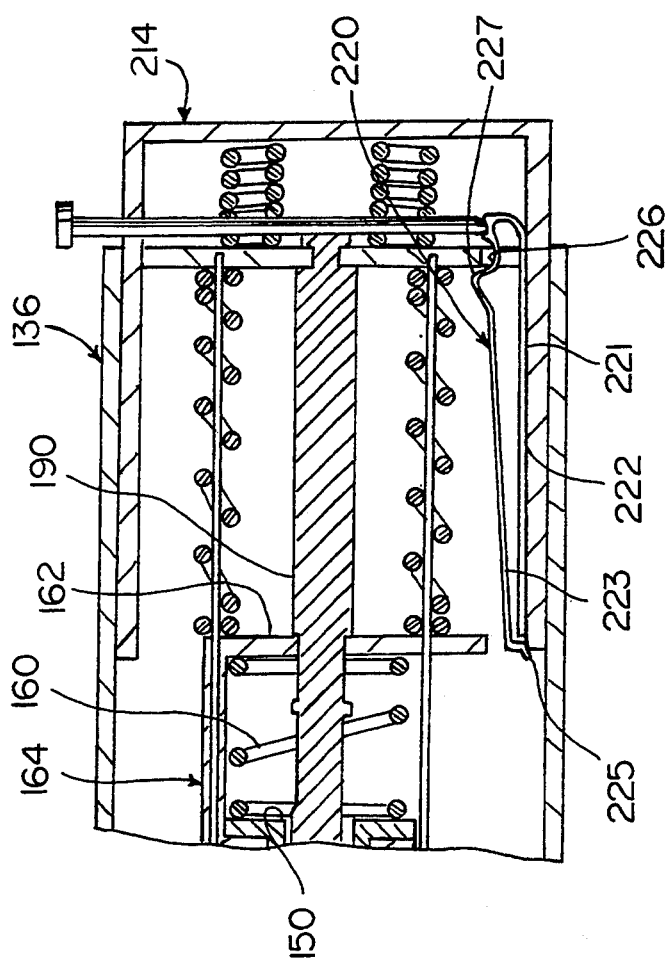
FIG. 19 is a broken side view, partly in longitudinal section, of the automatic retractable safety penetrating instrument of FIG. 17 in the extended position just prior to penetrating tissue.
Figure 20:
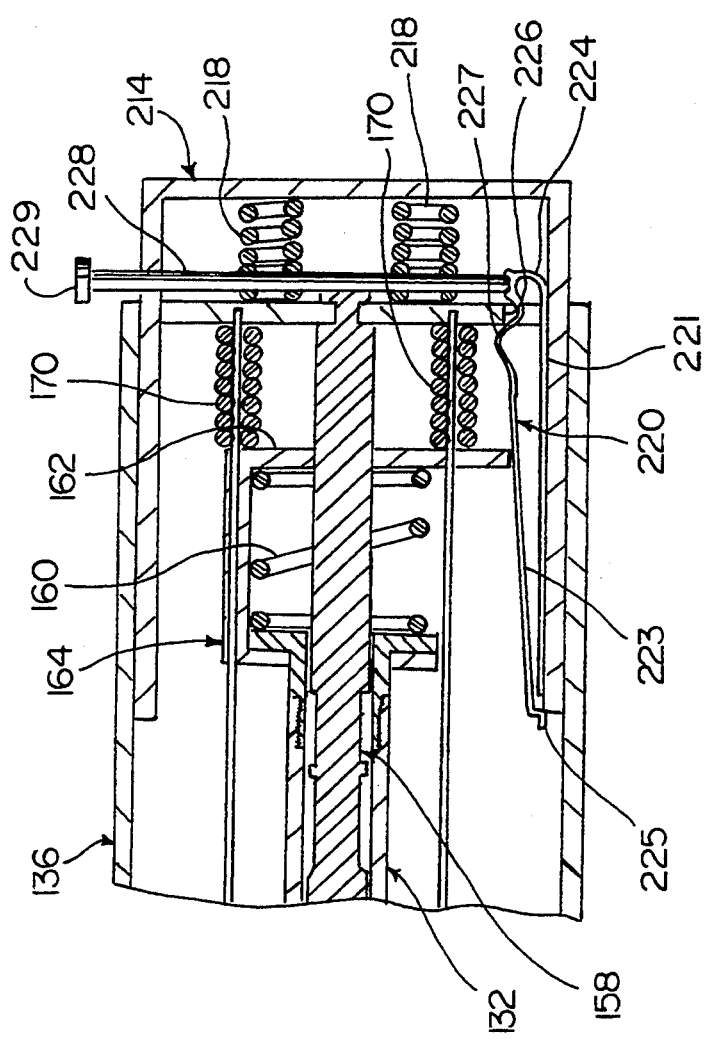
FIG. 20 is a broken side view, partly in longitudinal section, of the automatic retractable safety penetrating instrument of FIG. 17 in a retracted position.

In use, the automatic retractable safety penetrating instrument 130 is normally provided in the rest state wherein the distal end of penetrating member 132 is retracted within the portal sleeve, the rest state coinciding with the retracted position for the penetrating member shown in FIG. 17. In the rest state, keys 190 are within the keyways, and the retracting springs 170 are in a relaxed state causing retraction member 164 to be moved proximally, longitudinally along the locking and releasing mechanism. Springs 218 are similarly in a relaxed state biasing the end cap 216 in a proximal direction with bump 227 disposed proximally of slot 226. Spring 221 is similarly in a relaxed state with push arm 223 biased in the direction of the instrument longitudinal axis such that push finger 225 engages retraction plate 162. When it is desired to utilize the instrument 130 to penetrate tissue, the hub and end cap are squeezed to move the end cap distally against the bias of springs 218 causing push arm 223, via engagement of finger 225 with retraction plate 162, to move the retracting mechanism distally. Once the retraction plate 162 has been moved by the push arm 223 distally past the keys 190, cams 198 will axially rotate the locking and releasing mechanism a first angular increment causing the keys to be angularly offset from the keyways such that the retraction plate is locked or held in place against distal ends of the keys in an extended position for the instrument as illustrated in FIG. 18. In the extended position, bump 227 of spring 221 remains within the end cap 214 proximally of the hub rear wall. Further squeezing of the hub and end cap causes bump 227 to be moved through slot 226 such that the hub rear wall engages the bump to pivot the push arm 223 in the direction of base 222, i.e., in a direction outwardly from the instrument axis, and out of the path of longitudinal movement of the retraction plate as shown in FIG. 19. The bump 227 will be disposed in hub 136 and held adjacent a distal face of the hub rear wall preventing proximal movement of the end cap. The instrument 130 is now ready to be utilized to penetrate tissue as previously described for instrument 30. During penetration of tissue, the penetrating member 132 will be moved proximally against the bias of the operating spring 160 at which time the penetrating member will be in an operative position with a distal end junction of the penetrating member aligned with the distal end of the portal sleeve, and the locking and releasing mechanism will be axially rotated by the cams a second angular increment with the retraction plate 162 remaining held in place due to the keys remaining not aligned with the keyways. Once the distal end of the instrument has penetrated through the tissue, operating spring 160 will move the penetrating member distally causing the cams to again axially rotate the locking and releasing mechanism a third angular increment to align keys 190 with the keyways. Accordingly, retracting springs 170 will automatically move the retracting member 164 and with it the penetrating member 132 to the retracted position with the spring 221 disposed out of the path of movement of the retracting mechanism as illustrated in FIG. 20. The instrument 130 can be returned to the rest position by depressing push button 229, causing release bar 228 to compress bend 224 allowing bump 227 to move proximally through slot 226 due to the bias of springs 218.

Various types of bias devices including magnetic bias devices can be utilized in addition to springs 218 to bias the end cap 214. Skirt 216 can be disposed within the hub 136, or the skirt can be disposed around, outside or externally of the hub as shown in dotted lines in FIG. 17. Various types of push members can be utilized with the instrument 130 to engage and move the retracting mechanism distally when setting the instrument in the extended position. Various cams as well as other devices can be used to move the push member out of the path of longitudinal movement of the retracting mechanism prior to penetrating tissue. The push member can be arranged on the end cap in many various ways to be mounted within or externally of the end cap, and the push member can be arranged to cooperate with various other portions of the instrument in addition to the retraction plate to set the instrument in the extended position. Various types of cams 227 can be utilized with the push member to move the push member to a position allowing retraction of the penetrating member and, where a spring 221 is utilized as the push member, the cam 227 can have a variety of configurations. The cam 227 can be formed integrally, unitarily with the push member as shown, or the cam can be formed separately from the push member. Various types of trigger mechanisms can be utilized in the instrument 130 to move the push member out of the path of movement. Many different types of release mechanisms can be utilized to release the push member from the hub and, where bar 228 is utilized, the bar can extend through a top wall of the skirt as shown or the bar can extend through a lateral or side wall of the skirt with a tapered configuration to compress the bend as the bar is moved further into the end cap.

Figure 21:
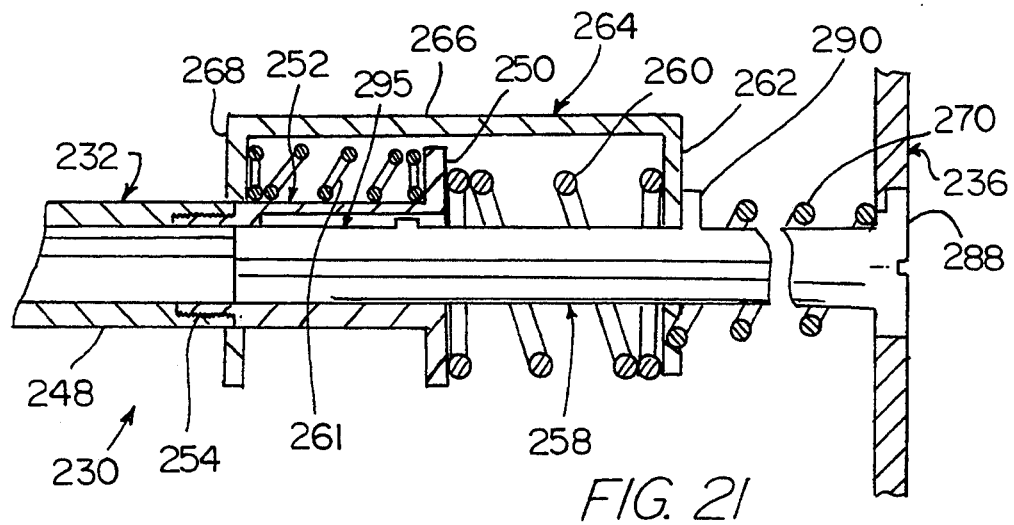
FIG. 21 is a broken side view, partly in longitudinal section, of another modification of the automatic retractable safety penetrating instrument according to the present invention in the extended position.
Figure 23:
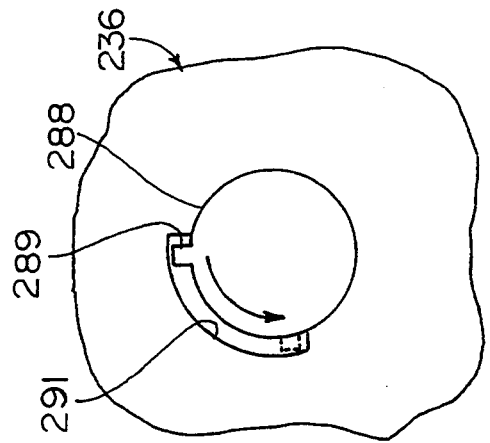
FIG. 23 is a broken end view of a rear wall of the hub of the automatic retractable safety penetrating instrument of FIG. 21.
Figure 24:
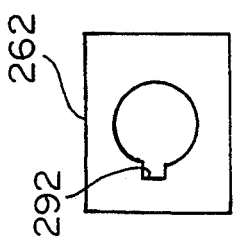
FIG. 24 is a proximal end view of the retraction plate of the automatic retractable safety penetrating instrument of FIG. 21.
Figure 25:
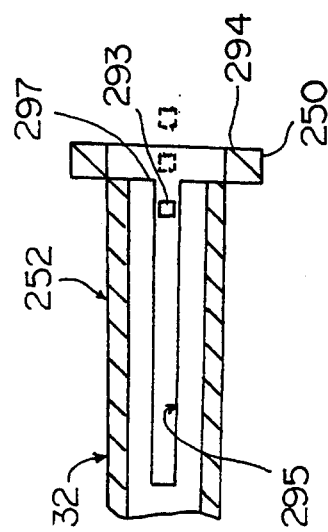
FIG. 25 is a broken, longitudinal sectional view of the penetrating member of the automatic retractable safety penetrating instrument of FIG. 21.
Figure 22:
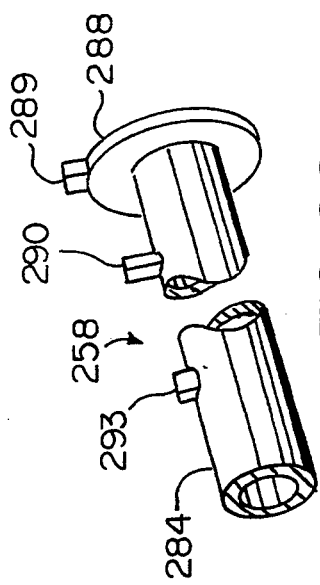
FIG. 22 is a perspective view of a locking and releasing mechanism of the automatic retractable safety penetrating instrument of FIG. 21.

Another modification of the automatic retractable safety penetrating instrument according to the present invention is illustrated at 230 in FIG. 21, only a portion of the penetrating unit for the instrument 230 being shown. The automatic retractable safety penetrating instrument 230 includes a portal unit as previously described and the penetrating unit including penetrating member 232 for being disposed within the portal sleeve of the portal unit and hub 236 mounting penetrating member 232. Penetrating member 232 is similar to penetrating member 32 and includes a body 248 terminating distally at a sharp tip for penetrating anatomical tissue and proximally at an end flange 250 at a proximal end 252 of the penetrating member, the proximal end being disposed in hub 236 with the body 248 passing through an aperture in a front wall (not shown) of the hub. The proximal end can be formed integrally, unitarily with the body 248 or the proximal end can be formed separately from the body and secured thereto in any suitable manner, such as with threads 254. A coiled helical operating spring 260 is connected between end flange 250 and a retraction plate 262 of the retracting member 264 to bias the penetrating member in a distal direction, the plate having an opening allowing passage therethrough of the locking and releasing mechanism 258 extending distally from a rear wall of the hub and into the proximal end of the penetrating member with the operating spring disposed concentrically around the locking and releasing mechanism. Retracting member 264 includes a side wall 266 extending distally from plate 262 to a forward wall 268 of the retracting member to form a recess for receiving the operating spring 260 and end flange 250 with the proximal end of the penetrating member passing through an opening in the forward wall 268. A retracting mechanism engages the proximal end of the penetrating member and includes retracting member 264 and a coiled helical retracting spring 270 connected between retraction plate 262 and the locking and releasing mechanism 258 to bias the retracting member in the proximal direction. The locking and releasing mechanism 258, shown in FIG. 22, actuates the retracting mechanism and includes a shaft 284 terminating proximally at a knob or flange 288 mounted in the rear wall of the hub to permit rotation of the locking and releasing mechanism. As shown in FIG. 23, a finger 289 on the knob 288 is mounted in an arcuate slot 291 formed in the hub rear wall to serve as a positive stop or abutment limiting rotation of the locking and releasing mechanism and for use in setting the instrument in an extended position as will be explained further below. If desired, the knob can be secured in the rear wall, in many various ways including the use of any suitable releasable detent preventing axial movement of the locking and releasing mechanism during use of the instrument in penetrating tissue while permitting the locking and releasing mechanism to be partially withdrawn from the instrument when setting the instrument in the extended position as will be explained further below. The locking and releasing mechanism 258 includes a locking member or protrusion 290 formed along the periphery of shaft 284 distally spaced from knob 288. As illustrated in FIG. 24, a slot or aperture 292 corresponding in configuration to the protrusion 290 is formed in retraction plate 262 along the opening receiving the locking and releasing mechanism to allow the retracting member to move longitudinally along the locking and releasing mechanism when the locking member 290 and the aperture 292 are longitudinally aligned. The retracting spring 270 is disposed concentrically around shaft 284 and is connected to the knob 288, the retracting spring being mounted in torsion to bias the locking and releasing mechanism rotationally as well as proximally. In the embodiment of FIG. 21, the retracting spring biases the locking and releasing mechanism rotationally in a counterclockwise direction when viewed distally from knob 288. A nub 293 is disposed along the periphery of shaft 284 distally spaced from locking member 290, and a longitudinal slot 295, best shown in FIG. 25, is formed along an inner diameter surface of the proximal end 252 of the penetrating member to receive nub 293 to prevent rotation of the locking and releasing mechanism due to the torsional bias of the retracting spring while allowing the penetrating member to move longitudinally along the locking and releasing mechanism when the nub is disposed within the slot as will be explained further below. Slot 295 has a proximal end 297 disposed distally of a proximal face 294 of end flange 250 such that the nub 293 can be disposed within the penetrating member between the slot proximal end and the proximal face of the end flange while being disengaged from the slot. A balancing or positioning spring 261, stronger than operating spring 260, is connected between end flange 250 and forward wall 268 to bias the penetrating member in the proximal direction against the distal bias of the operating spring to position the penetrating member with nub 293 engaged in slot 295 in the extended position for the instrument 230 as will be described below.

Figure 26:
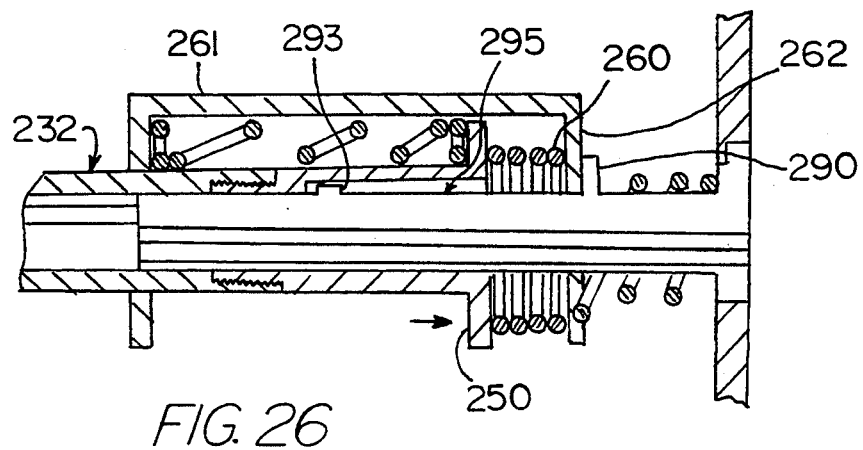
FIG. 26 is a broken side view, partly in longitudinal section, of the automatic retractable safety penetrating instrument of FIG. 21 in the operative position during penetration of tissue.
Figure 27:
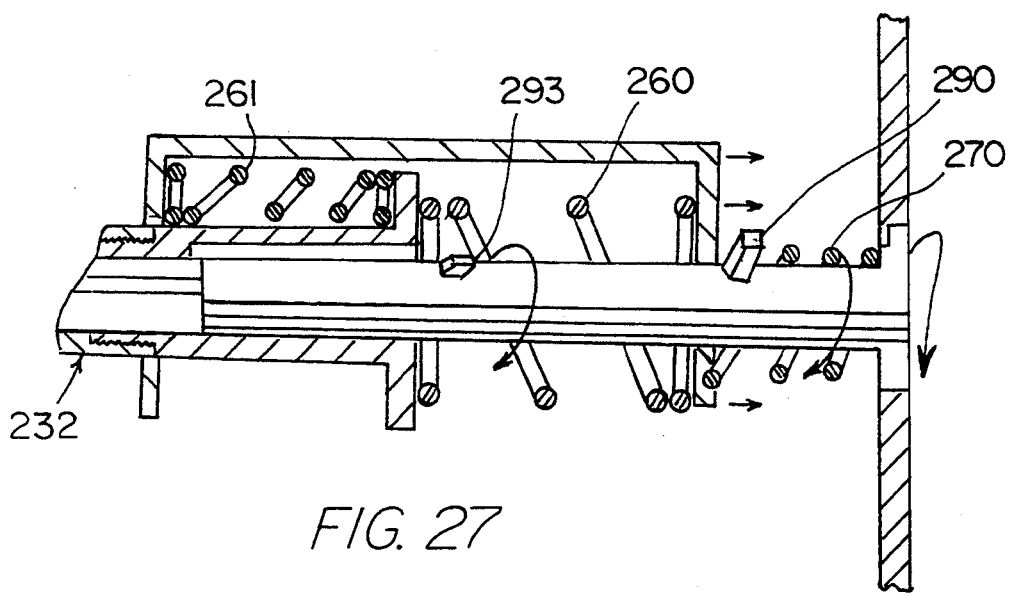
FIG. 27 is a broken side view, partly in longitudinal section, of the automatic retractable safety penetrating instrument of FIG. 21 upon penetration through the tissue.

In use, the penetrating unit of the automatic retractable safety penetrating instrument 230 is coupled with the portal unit with the penetrating member 232 disposed within the portal sleeve of the portal unit. The instrument is preferably provided in a rest state with the operating, retracting and positioning springs provided in rest, unbiased or relaxed states. In the rest state, nub 293 is disposed proximally of and, therefore, disengaged from slot 295, and the locking and releasing mechanism 258 is rotated by the retracting spring 270 such that the locking member 290 is aligned with the slot or aperture 292, the finger 289 engaging a lower end of the slot 291 to serve as a positive stop or abutment limiting rotation of the locking and releasing mechanism as shown by the dotted lines in FIG. 23. The retracting member 264 and with it the penetrating member 232 will be moved proximally to a retracted position for the penetrating member due to the proximal bias of the retracting spring with the locking member 290 disposed distally of the retraction plate 262. Accordingly, in the rest state, the sharp tip of the penetrating member will be disposed within the portal sleeve in a safe, protected position. When it is desired to utilize the instrument 230 to penetrate tissue, knob 288 is grasped and pulled proximally, partially withdrawing the locking and releasing mechanism from the hub to move the locking member 290 through the aperture 292 to be disposed proximally of the retraction plate 262. The knob 288 is rotated clockwise to position the finger 289 at an upper end of the slot 291 such that the locking member 290 is no longer aligned with the aperture 292 in the retraction plate and the nub 293 is longitudinally aligned with the slot 295. The knob is moved distally and replaced in the hub rear wall causing the retracting member 264, via engagement of the locking member 290 with retraction plate 262, to be moved distally. The penetrating member is moved distally with the retracting member causing the nub 193 to be moved into the longitudinal slot 295 in the extended condition for the instrument illustrated in FIG. 21. In the extended condition, the junction joining the sharp tip of the penetrating member to the body 248 is disposed distally of a distal end of the portal sleeve, the retraction plate 262 is held against movement by the locking member 290 and the locking and releasing mechanism is prevented from rotating by nub 293 engaged in slot 295 with the balancing spring 261 positioning the penetrating member against the bias of the operating spring in a balanced position maintaining the slot in engagement with the nub. The instrument can now be utilized to penetrate tissue and enter an anatomical cavity. The hub and housing are grasped by the surgeon, and the instrument is forced against tissue causing penetrating member 232 to move proximally against the bias of operating spring 260 at which time the penetrating member will be in the operative position with the distal end junction of the penetrating member aligned with the distal end of the portal sleeve, and the slot 295 will be moved proximally such that the nub 293 will be disposed toward a distal end of the slot 295 as shown in FIG. 26 while the retraction plate 262 remains held by the locking member 290. Once the distal end of the instrument has passed through the tissue, operating spring 260 will move penetrating member 232 distally, and the momentum of the operating spring will temporarily override the bias of the positioning spring 261 such that the penetrating member is moved distally of the balanced position established by spring 261 causing the longitudinal slot to be moved distally of and, therefore, disengaged from, the nub as illustrated in FIG. 27. Depending upon the momentum of the operating spring, the nub can remain within the penetrating member when the slot 295 is moved distally or the nub can be disposed externally of the penetrating member as illustrated by the two dotted line positions in FIG. 25. Accordingly, the penetrating member with slot 295 functions as the operating member with the nub being released from the slot upon distal movement of the penetrating member upon penetration through the tissue, and retracting spring 270 will automatically rotate the locking and releasing mechanism counterclockwise to align the locking member 290 with the aperture 292 with the finger 289 being moved to the lower end of slot 291 to limit rotation of the locking and releasing mechanism. With the locking member and aperture aligned, the retracting spring will automatically move the retracting member and with it the penetrating member to the retracted position, the retracted position corresponding to the rest state with the sharp distal tip of the penetrating member within the portal sleeve in a safe protected position.

Figure 28:
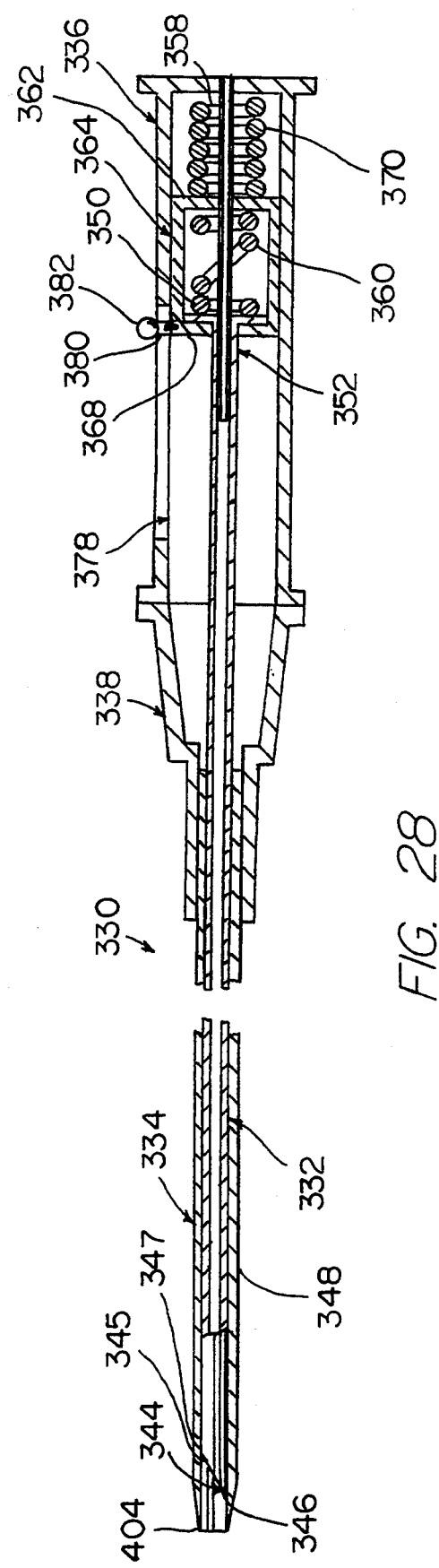
FIG. 28 is a broken side view, partly in longitudinal section, of an additional modification of the automatic retractable safety penetrating instrument according to the present invention in the retracted position.

Another modification of the automatic retractable safety penetrating instrument according to the present invention is illustrated at 330 in FIG. 28. Automatic retractable safety penetrating instrument 330 includes an elongate penetrating member such as a needle 332, an outer sleeve such as a catheter 334 concentrically disposed around the needle, a barrel 336 mounting needle 332 and a fitting 338 mounting catheter 334. The barrel can be latched to the fitting with the use of any suitable releasable mechanism or the needle can be frictionally retained in the catheter allowing the barrel to be removed from the fitting withdrawing the needle from the catheter. Accordingly, the automatic retractable safety penetrating instrument 330 can be considered to be formed of a catheter unit and a needle unit, the catheter unit including catheter 334 and fitting 338 and the needle unit including needle 332 and barrel 336.

Figure 29:
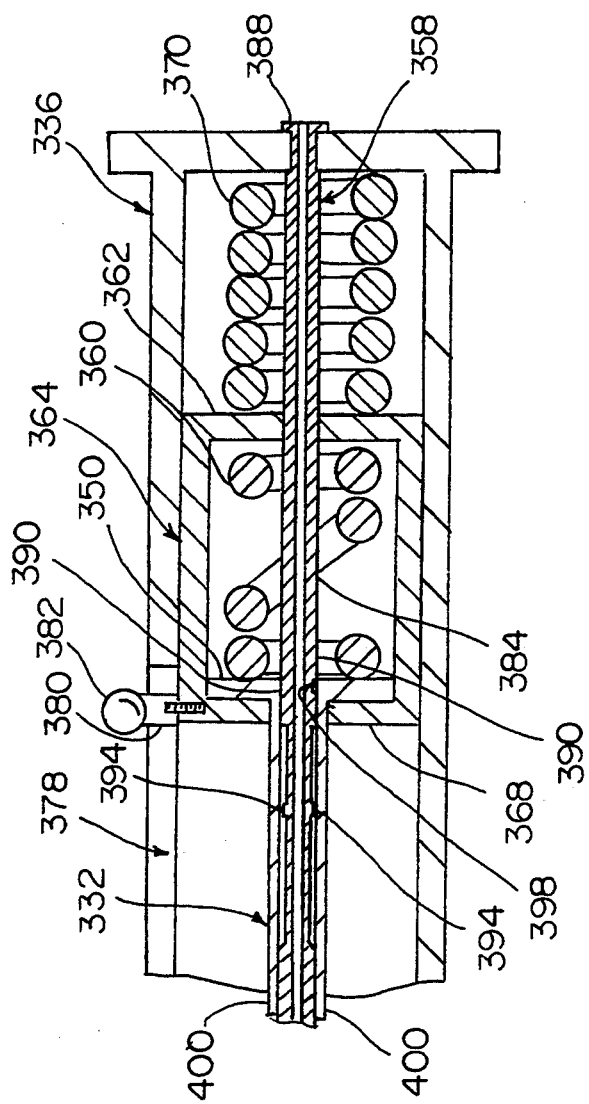
FIG. 29 is a broken side view, partly in longitudinal section, of the barrel of the automatic retractable safety penetrating instrument of FIG. 28.

Needle 332 is preferably made of a medical grade material, such as stainless steel, and has an outer diameter or size dependent upon the surgical procedure to be performed with the needle typically being sized for intravenous use. The needle 332 has a distal end 344 terminating at a sharp tip 346 for penetrating anatomical tissue. The distal end 344 can have various configurations; and, as shown in FIG. 28, the distal end is formed with an acutely angled edge 345 terminating proximally at junction 347 joining the edge to an elongate body 348. By forming the needle distal edge to be curved in the direction of a longitudinal axis of the instrument 330, a scooping or curving motion can be utilized when penetrating tissue. Body 348 extends proximally from junction 347 to terminate at an end flange 350 at a proximal end 352 of the needle, the proximal end being disposed in barrel 336. Body 348 is hollow or cannulated along the length of the needle to communicate with an opening circumscribed by the acutely angled distal edge and to receive a locking and releasing mechanism 358 extending distally from a rear wall of the barrel and into the proximal end of the needle. As best illustrated in FIG. 29, a coil helical operating spring 360 is connected between end flange 350 and a retraction plate 362 of retracting member 364, the plate having an opening allowing passage therethrough of the locking and releasing mechanism 358 with the operating spring disposed concentrically around the locking and releasing mechanism. Retracting member 364 defines an enclosure or structure for receiving the operating spring 360 and end flange 350 with the proximal end of the penetrating member passing through a slot or opening in a forward wall 368 of the retracting member. A retracting spring 370 is connected between retraction plate 362 and the rear wall of the barrel, the retracting spring being disposed concentrically around the locking and releasing mechanism 358.

Barrel 336 can be made of any suitable material, a preferred material for the barrel being plastic to allow the barrel to be disposable for single patient use. Barrel 336 can have any desired configuration in cross-section and is shown in FIG. 28 as being substantially cylindrical with an open forward end allowing passage therethrough of the needle 332. A longitudinal slot 378 is disposed in the cylindrical wall of the barrel in alignment with a longitudinal axis of the instrument 330. A pin 380 is threadedly secured to the retracting member 364, the pin being secured in the periphery of forward wall 368 of the retracting member. Pin 380 extends through slot 378 and terminates at an external knob 382.

Locking and releasing mechanism 358, best illustrated in FIG. 29, is similar to locking and releasing mechanism 58 and includes shaft 384, keys 390 for being received in keyways in retraction plate 362 and projections 394 and ribs 400 for cooperating with operating members or cams 398 on the needle to rotate the locking and releasing mechanism. Shaft 384 of the locking and releasing mechanism is hollow to communicate with the lumen of the needle to allow passage of fluid entirely through the instrument, and end flange 388 of the locking and releasing mechanism can be provided with a valve to control fluid flow through the instrument. If desired, a control tube can be disposed in shaft 384 with the value communicating with the lumen of the control tube as previously described.

Catheter 334 is preferably made of a substantially cylindrical length of flexible material and has an outer diameter typically sized for intravenous use. The catheter has a distal end 404 that can have a configuration to produce a smooth profile with the angled distal edge of the needle when the instrument is in an operative position to penetrate tissue and a proximal end mounted in or formed with barrel 338 with a lumen extending between the distal and proximal ends. Fitting 338 can be made of any suitable material to be disposable and has a tapered configuration to facilitate grasping during use. Fitting 338 has an open rear end communicating with the open forward end of the barrel and an open forward end allowing passage therethrough by the needle.

In use, the automatic retractable safety penetrating instrument 330 is normally provided in a rest state wherein the distal end 344 of the needle is retracted within the catheter to be in a safe, protected position, the rest state coinciding with the retracted position for the needle shown in FIGS. 28 and 29. In the rest state, the keys are within the keyways causing retraction member 364 to be moved by the retracting spring 370 proximally, longitudinally along the locking and releasing mechanism carrying with it the needle such that pin 380 is disposed at a proximal end of slot 378. When it is desired to utilize the instrument 330 to penetrate tissue to introduce the catheter into an anatomical cavity such as a vein, knob 382 is grasped and moved distally within slot 378 causing retracting member 364 to move distally along the locking and releasing mechanism due to the keys being received in the keyways. The needle and, therefore, the cams, are moved distally with the retracting member, the cams contacting the ribs to axially rotate the locking and releasing mechanism. Upon rotation of the locking and releasing mechanism 358, the keys will be angularly offset from the keyways such that the retraction plate 362 will be held or locked in place against the keys. With the instrument 330 in the extended position, the distal end junction 347 of the needle will be distally spaced from the distal end 404 of the catheter. The instrument can now be utilized to penetrate tissue and enter an anatomical cavity. The fitting and barrel are grasped, and the instrument is forced against tissue forming a wall of an anatomical cavity causing the needle to move proximally against the bias of operating spring 360 at which time the needle will be in an operative position with the junction 347 aligned with the distal end 404 of the catheter to form a substantially smooth profile. As the needle moves proximally during penetration of the tissue, the cams move proximally into engagement with the projections to axially rotate the locking and releasing mechanism an additional increment. Upon rotation of the locking and releasing mechanism the additional increment, the keys remain angularly offset and not aligned with the keyways such that the retraction plate remains held in place. Once the distal end of the catheter has passed through the tissue, operating spring 360 will move the needle distally causing the cams to be moved distally into engagement with the ribs such that the locking and releasing mechanism is again axially rotated to align the keys with the keyways and release the retracting mechanism. Retracting springs 370 will automatically move the retracting member 364 and with it the needle 332 to a retracted position corresponding to the rest position shown in FIG. 28 with the sharp distal tip of the needle in a safe protected position. Once the needle has moved to the retracted position, fluids can be introduced or withdrawn from the body cavity via the lumens of the needle and the locking and releasing mechanism or the needle unit can be withdrawn from the catheter unit allowing the fitting to be connected with various devices for aspirating or introducing fluids into the anatomical cavity via the catheter unit. Where the needle unit is withdrawn, the needle can be moved into a protective safety sheath or housing such that the sharp tip of the needle is protected upon withdrawal.

Figure 30:
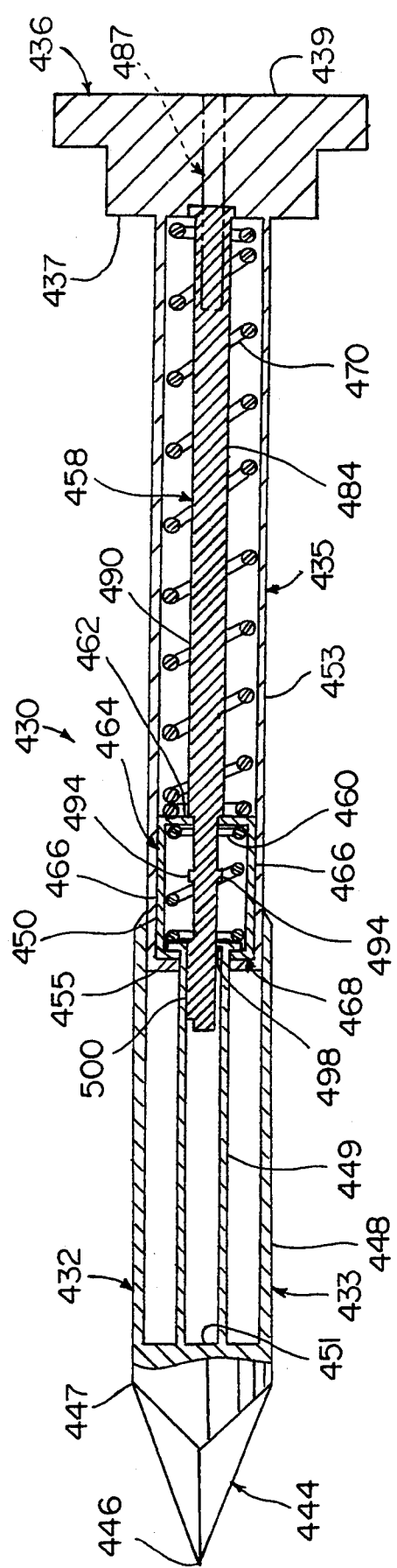
FIG. 30 is a side view, partly in longitudinal section, of a further modification of the automatic retractable safety penetrating instrument according to the present invention.

A further modification of the automatic retractable safety penetrating instrument according to the present invention is illustrated in FIG. 30 at 430, only the penetrating member unit for the instrument 430 being shown. Instrument 430 includes a portal unit and the penetrating unit including a penetrating member 432 for being received in a portal sleeve of the portal unit and a hub 436 mounting penetrating member 432. Penetrating member 432 is formed of a distal part 433 in telescoping arrangement with an intermediate or end part 435 with distal part 433 having a distal end 444 including a plurality of facets terminating distally at a sharp tip 446 for penetrating anatomical tissue and proximally at a junction 447 joining the facets to an elongate, outer tubular body 448. Body 448 is concentrically disposed around an inner tubular member 449 extending proximally from an internal end wall or shoulder 451 disposed in body 448 transverse to a longitudinal axis of the instrument, the inner tubular member terminating proximally at an end flange 450 disposed in a retracting member 464. A tubular body 453 of intermediate penetrating member part 435 has a distal end disposed in outer body 448 and a proximal end joined to or formed as part of hub 436. Body 453 terminates distally at a transverse forward wall 455 disposed in outer body 448, the forward wall having a slot or opening allowing passage therethrough by the inner tubular member 449. Retracting member 364 is disposed in the intermediate body 453 and includes a retraction plate 462, a pair of opposing side walls 466 extending in a distal direction from retraction plate 462 and a forward wall 468 distally joined to side walls 466 with the forward wall having a slot or opening allowing passage therethrough by the inner tubular member 449. Retracting member 464 defines an enclosure or structure for receiving the end flange 450 and an operating spring 460 connected between the end flange and the retraction plate 462 to mount the outer body for telescoping movement along the intermediate body. A locking a releasing mechanism 458 disposed within the outer and intermediate bodies of the penetrating member extends distally from a forward wall 437 of hub 436 to extend through intermediate body 453 and into the inner tubular member 449, the locking and releasing mechanism extending through an opening in the retraction plate 462. A retracting spring 470 is connected between retraction plate 462 and the forward wall 437 of the hub, the retracting and operating springs being disposed concentrically around the locking and releasing mechanism. Locking and releasing mechanism 458 is similar to locking and releasing mechanism 58 and includes shaft 484 which can be solid or hollow, keys 490 for being received in keyways in retraction plate 462 and projections 494 and ribs 500 for cooperating with operating members or cams 498 on the inner tubular member 449 of the penetrating member to rotate the locking and releasing mechanism. Where shaft 484 is hollow to communicate with the lumen of the inner tubular member, a passage can be formed through the distal end 444 of the penetrating member in alignment with the inner tubular member lumen, and a control tube 487 illustrated in dotted lines in FIG. 30 can be disposed in the lumen of the shaft to extend through the hub to provide fluid communication entirely through the instrument 430. A valve, which can be of any conventional type, can be provided in communication with the control tube, such as along a rear wall 439 of the hub, to control fluid flow through the instrument. It will be appreciated that the locking and releasing mechanism can be disposed entirely within the penetrating member 432 depending upon the structure utilized to rotatably mount the locking and releasing mechanism at the forward wall of the hub, within the penetrating member or on control tube 487. Hub 436 can have any configuration in cross section to facilitate grasping, it being noted that the instrument 430 is particularly advantageous where it is desirable to greatly reduce the size of the hub such that the hub can have a minimal length, width and height and can be formed as an extension or continuation of the intermediate body 453. Various devices can be provided in the instrument 430 for moving the retracting mechanism when setting the instrument in an extended position as will be explained below and an opening or hole can be provided in the hub to allow the instrument to be set from the proximal end by pushing the retracting mechanism.

In use, the penetrating unit is combined with the portal unit with the penetrating member 432 concentrically disposed in the portal sleeve of the portal unit. Depending upon the structure provided for setting the instrument in the extended position, the instrument 430 can be provided in a rest state wherein the distal end 444 of the penetrating member is retracted within the portal sleeve to be in a safe, protected position or the instrument can be supplied in the extended position with the distal end 444 disposed beyond the distal end of the portal sleeve. In the rest state, the keys 490 are within the keyways in the retraction plate 462 causing retraction member 464 to be moved by the retracting spring 470 proximally, longitudinally along the locking and releasing mechanism carrying with it the penetrating member. When it is desired to utilize the instrument 430 to penetrate tissue to introduce the portal sleeve into an anatomical cavity, the retracting member 464 is manually moved distally within the intermediate body 453 causing retracting member 464 to move distally along the locking and releasing mechanism 458 due to the keys being received in the keyways. Accordingly, the distal part 433 will be moved distally relative to the intermediate part 435 causing the cams to contact the ribs 500 to axially rotate the locking and releasing mechanism. Upon rotation of the locking and releasing mechanism, the keys 490 will be angularly offset from the keyways such the retraction plate 462 will be held or locked in place against distal ends of the keys as illustrated in FIG. 30. With the instrument 430 in the extended position, the distal end junction 447 of the penetrating member will be distally spaced from the distal end of the portal sleeve. The instrument can now be utilized to penetrate tissue and enter an anatomical cavity. The hub 336 is grasped, and the instrument is forced against tissue forming a wall of an anatomical cavity causing the distal part 433 to move proximally against the bias of operating spring 460 relative to the intermediate part 435 at which time the penetrating member will be in an operative position with the junction 447 aligned with the distal end of the portal sleeve to form a substantially smooth profile. As the distal part 433 moves proximally during penetration of the tissue, the cams 498 move proximally into engagement with the projections 494 to axially rotate the locking and releasing mechanism an additional increment. Upon rotation of the locking and releasing mechanism the additional increment, the keys 490 remain angularly offset and not aligned with the keyways such that the retraction plate 362 remains held in place. Once the distal end of the portal sleeve has passed through the tissue, operating spring 460 will move the distal part 433 distally relative to the intermediate part 435 causing the cams 498 to be moved distally into engagement with the ribs 500 such that the locking and releasing mechanism is again axially rotated to align the keys with the keyways and release the retracting mechanism. Retracting spring 470 will automatically move the retracting member 464 and with it the distal part 433 to a retracted position corresponding to the rest position with the sharp distal tip of the penetrating member in a safe protected position.

Thus, it will be appreciated that in automatic safety penetrating instrument 430 the shaft of the penetrating member is formed of telescoping parts such that the distal end 444 is retracted by telescoping proximal movement of the distal part 433 of the penetrating member relative to the intermediate part 435 of the penetrating member whereby hub 436 need not house any mechanisms and need not provide any longitudinal space for retraction of the penetrating member distal end. Retracting spring 470 retracts the distal end 444 until shoulder 451 abuts wall 455 such that the distal end 444 is within the portal sleeve, and the sliding or telescoping movement between the parts of the penetrating member can be accomplished with other structural arrangements, for example by eliminating tubular body 448 to permit distal part 433 to telescope only within intermediate part 435.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An automatic retractable safety penetrating instrument for introducing a sleeve into a cavity in the body comprising sleeve means for providing a passage through a cavity wall and having a distal end for positioning in the body cavity, a proximal end for positioning externally of the body cavity and a lumen extending between said distal and proximal sleeve means ends;

a penetrating member disposed in said lumen of said sleeve means and having a longitudinal axis and a sharp distal end for penetrating the cavity wall;

retracting means for moving said sharp distal end of said penetrating member proximally relative to said sleeve means from an extended position where said sharp distal end protrudes beyond said sleeve means distal end to a retracted position to prevent contact of said sharp distal end with tissue; and locking and releasing means mounted for axial rotation relative to said penetrating member and about said longitudinal axis for automatically actuating said retracting means to move said sharp distal end of said penetrating member to the retracted position in response to axial rotation of said locking and releasing means automatically upon said sleeve means distal end entering the body cavity.

2. An automatic retractable safety penetrating instrument as recited in claim 1 wherein said retracting means includes a retracting member for carrying said penetrating member and biasing means for biasing said retracting member in a proximal direction.

3. An automatic retractable safety penetrating instrument as recited in claim 2 wherein said locking and releasing means includes means for preventing movement of said retracting member in the proximal direction in the extended position.

4. An automatic retractable safety penetrating instrument as recited in claim 3 wherein said retracting member includes a retraction plate having an opening therein receiving said locking and releasing means and said movement preventing means includes protrusion means on said locking and releasing means for engaging said retraction plate in the extended position.

5. An automatic retractable safety penetrating instrument for introducing a sleeve into a cavity in the body comprising a sleeve for providing a passage through a cavity wall and having a distal end for positioning in the body cavity, a proximal end for positioning externally of the body cavity and a lumen extending between said distal and proximal sleeve ends;

a penetrating member disposed in said lumen of said sleeve and having a longitudinal axis and a sharp distal end for penetrating the cavity wall;

retracting means for moving said sharp distal end of said penetrating member proximally relative to said sleeve from an extended position where said sharp distal end protrudes beyond said sleeve distal end to a retracted position to prevent contact of said sharp distal end with tissue, said retracting means including a retracting member for carrying said penetrating member and biasing means for biasing said retracting member in a proximal direction;

locking and releasing means rotatable about said longitudinal axis for automatically actuating said retracting means to move said sharp distal end of said penetrating member to the retracted position in response to axial rotation of said locking and releasing means upon said sleeve distal end entering the body cavity, said locking and releasing means including means for preventing movement of said retracting member in the proximal direction in the extended position, said retracting member including a retraction plate having an opening therein receiving said locking and releasing means, said movement preventing means including protrusion means on said locking and releasing means for engaging said retraction plate in the extended position; and slot means in said retraction plate along said opening for being aligned with said protrusion means upon rotation of said locking and releasing means in response to said sleeve distal end entering the body cavity to permit movement of said retracting member in the proximal direction.

6. An automatic retractable safety penetrating instrument as recited in claim 5 and further comprising distally movable operating means for axially rotating said locking and releasing means automatically to align said protrusion means with said slot means in response to distal movement of said operating means upon said sleeve distal end entering the body cavity.

7. An automatic retractable safety penetrating instrument as recited in claim 6 and further comprising means for biasing said penetrating member in a distal direction to the extended position with said sharp distal end disposed distally of said sleeve distal end, said distal biasing means permitting said sharp distal end to move in a proximal direction to an operative position during penetration of the cavity wall and in a distal direction from the operative position toward the extended position upon said sleeve distal end entering the body cavity.

8. An automatic retractable safety penetrating instrument as recited in claim 7 wherein said operating means includes cam means on said penetrating member and further including contact means on said locking and releasing means for being engaged by said cam means to rotate said locking and releasing means.

9. An automatic retractable safety penetrating instrument as recited in claim 8 wherein said slot means includes at least two slots and said protrusion means includes at least one protrusion aligned with one of said slots in the retracted position and further comprising means for manually moving said penetrating member from the retracted position to the extended position.

10. An automatic retractable safety penetrating instrument as recited in claim 9 wherein said contact means includes rib means for being engaged by said cam means to axially rotate said locking and releasing means a first increment to position said protrusion in engagement with said retraction plate at a first angular position between said slots when said penetrating member is manually moved from the retracted position to the extended position.

11. An automatic retractable safety penetrating instrument as recited in claim 10 wherein said contact means includes projection means for being engaged by said cam means to axially rotate said locking and releasing means a second increment to position said protrusion in engagement with said retraction plate at a second angular position between said first position and the other of said slots when said penetrating member is moved to the operative position.

12. An automatic retractable safety penetrating instrument as recited in claim 11 wherein said rib means is engaged by said cam means to axially rotate said locking and releasing means a third angular increment to align said protrusion with said other of said slots when said penetrating member is moved toward the extended position upon said sleeve distal end entering the body cavity.

13. An automatic retractable safety penetrating instrument as recited in claim 12 wherein said protrusion means includes four protrusions disposed at 90° spaced locations and said slot means includes four slots disposed at 90° spaced locations.

14. An automatic retractable safety penetrating instrument as recited in claim 13 wherein said projection means includes four projections disposed at 90° spaced locations longitudinally aligned with said protrusions, said rib means includes four ribs disposed at 90° spaced locations angularly offset from said projections and said cam means includes four cams disposed at 90° spaced locations for being longitudinally aligned with said ribs in the retracted and operative positions and with said projections in the extended position.

15. An automatic retractable safety penetrating instrument as recited in claim 13 wherein said first, second and third angular increments are each 30°.

16. An automatic retractable safety penetrating instrument as recited in claim 7 wherein said proximal biasing means includes means for rotating said locking and releasing means automatically upon said sleeve distal end entering the body cavity.

17. An automatic retractable safety penetrating instrument as recited in claim 16 wherein said proximal biasing means and said rotating means include a single spring mounted in torsion between said retracting member and said locking and releasing means.

18. An automatic retractable safety penetrating instrument as recited in claim 17 wherein said locking and releasing means includes means for preventing axial rotation of said locking and releasing means in the extended and operative positions.

19. An automatic retractable safety penetrating instrument as recited in claim 18 wherein said locking and releasing means includes a shaft disposed in said penetrating member and said rotation preventing means includes a nub on said shaft and a slot in said penetrating member for engaging said nub.

20. An automatic retractable safety penetrating instrument as recited in claim 19 and further comprising means for biasing said penetrating member in a proximal direction in opposition to said distal biasing means for positioning said slot to engage said nub in the extended and operative positions.

21. An automatic retractable safety penetrating instrument as recited in claim 1 wherein said penetrating member includes a proximal end and an elongate shaft between said penetrating member distal and proximal ends and said locking and releasing means is disposed substantially entirely within said shaft.

22. An automatic retractable safety penetrating instrument as recited in claim 1 wherein said penetrating member is formed of first and second telescoping parts, said first part carrying said sharp distal end and being movable proximally relative to said second part to move said sharp distal end to the retracted position.

23. An automatic retractable safety penetrating instrument as recited in claim 1 wherein said sleeve means includes a portal sleeve and said penetrating member includes a trocar.

24. An automatic retractable safety penetrating instrument as recited in claim 1 wherein said sleeve means includes a catheter and said penetrating member includes a needle.

25. An automatic retractable safety penetrating instrument as recited in claim 1 and further comprising means for manually moving said penetrating member from the retracted position to the extended position.

26. An automatic retractable safety penetrating instrument as recited in claim 25 wherein said penetrating member includes a proximal end and further comprising a hub mounting said penetrating member proximal end and wherein said moving means includes a pin for being moved in a distal direction along a longitudinal slot in said hub.

27. An automatic retractable safety penetrating instrument as recited in claim 26 wherein said retracting means includes a retracting member, for carrying said penetrating member and said pin is mounted on said retracting member.

28. An automatic retractable safety penetrating instrument as recited in claim 25 wherein said penetrating member includes a proximal end and further comprising a hub mounting said penetrating member proximal end and wherein said moving means includes a push member and an end cap on said hub for moving said push member in a distal direction.

29. An automatic retractable safety penetrating instrument as recited in claim 28 wherein said push member includes a push arm extending through a slot in said hub.

30. An automatic retractable safety penetrating instrument as recited in claim 29 and further including a push finger on said push arm for engaging said retracting means.

31. An automatic retractable safety penetrating instrument as recited in claim 30 and further including bias means for mounting said end cap for movement relative to said hub to move said push member in response to distal movement of said end cap.

32. An automatic retractable safety penetrating instrument as recited in claim 31 and further including cam means for being moved distally through said slot in response to distal movement of said end cap to move said push arm out of engagement with said retracting means once said penetrating member has been moved to the extended position.

33. An automatic retractable safety penetrating instrument as recited in claim 32 wherein said cam means is automatically held in said hub upon movement of said cam means distally through said slot.

34. An automatic retractable safety penetrating instrument as recited in claim 33 and further including means for releasing said cam means from said hub.

35. An automatic retractable safety penetrating instrument as recited in claim 34 wherein said push member includes a spring and said cam means includes a bump on said spring.

36. An automatic retractable safety penetrating instrument as recited in claim 35 wherein said spring includes a base and a bend joining said base to said push arm and said releasing means includes a movable release bar extending into said end cap for compressing said bend to allow said cam means to move proximally through said slot in response to movement of said release bar against said bend.

37. An automatic retractable safety penetrating instrument as recited in claim 36 wherein said release bar includes a button disposed externally of said end cap for moving said release bar against said bend.

38. An automatic retractable safety penetrating instrument as recited in claim 37 wherein said mounting bias means includes a spring.

39. An automatic retractable safety penetrating instrument as recited in claim 1 wherein said locking and releasing means includes a hollow shaft and further including a control tube disposed in said shaft.

* * * * *